US009379336B2

United States Patent
Sisk

(10) Patent No.: US 9,379,336 B2
(45) Date of Patent: Jun. 28, 2016

(54) COMPOUNDS FOR USE IN LIGHT EMITTING DEVICES

(71) Applicant: Nitto Denko Corporation, Osaka (JP)

(72) Inventor: David T. Sisk, San Diego, CA (US)

(73) Assignee: NITTO DENKO CORPORATION, Osaka (JP)

( * ) Notice: Subject to any disclaimer, the term of this patent is extended or adjusted under 35 U.S.C. 154(b) by 320 days.

(21) Appl. No.: 13/975,959

(22) Filed: Aug. 26, 2013

(65) Prior Publication Data

US 2014/0061614 A1    Mar. 6, 2014

Related U.S. Application Data

(60) Provisional application No. 61/695,711, filed on Aug. 31, 2012.

(51) Int. Cl.
| | |
|---|---|
| *H01L 51/00* | (2006.01) |
| *C09K 11/06* | (2006.01) |
| *H05B 33/14* | (2006.01) |
| *C07D 401/14* | (2006.01) |
| *C07D 403/10* | (2006.01) |

(52) U.S. Cl.
CPC .......... *H01L 51/0072* (2013.01); *C07D 401/14* (2013.01); *C07D 403/10* (2013.01); *C09K 11/06* (2013.01); *H01L 51/0052* (2013.01); *H01L 51/0067* (2013.01); *H05B 33/14* (2013.01); *C09K 2211/1007* (2013.01); *C09K 2211/1011* (2013.01); *C09K 2211/1029* (2013.01); *C09K 2211/1033* (2013.01); *C09K 2211/1037* (2013.01); *H01L 51/0037* (2013.01); *H01L 51/0059* (2013.01); *H01L 51/0085* (2013.01); *H01L 2251/308* (2013.01)

(58) Field of Classification Search
None
See application file for complete search history.

(56) References Cited

U.S. PATENT DOCUMENTS

| | | |
|---|---|---|
| 2007/0205412 A1 | 9/2007 | Bae et al. |
| 2009/0134783 A1 | 5/2009 | Lin |
| 2010/0326526 A1 | 12/2010 | Zheng et al. |
| 2011/0140093 A1 | 6/2011 | Zheng et al. |

FOREIGN PATENT DOCUMENTS

| | | |
|---|---|---|
| JP | 2001023777 | 1/2001 |
| KR | 2009073852 | 7/2009 |
| KR | 2011047803 | 5/2011 |
| WO | 2007-046658 A1 | 6/2007 |

(Continued)

OTHER PUBLICATIONS

G. Gustafsson, et al., "Flexible light-emitting diodes made from soluble conducting polymers," Nature, vol. 357, No. 6378, pp. 477-479, 1992.

(Continued)

*Primary Examiner* — J. L. Yang
(74) *Attorney, Agent, or Firm* — K&L Gates LLP; Brent A. Johnson; Louis C. Cullman

(57) ABSTRACT

Optionally substituted ambipolar naphthalene compounds useful in light-emitting devices are described, including without limitation 9-(3-(10-(3-(1-phenyl-1H-benzo[d]imidazol-2-yl)phenyl)anthracen-9-yl)phenyl)-9H-carbazole and 9-(3-(10-(3-(1-phenyl-1H-benzo[d]imidazol-2-yl)phenyl) anthracen-9-yl)phenyl)-9H-carbazole.

20 Claims, 1 Drawing Sheet

(56) References Cited

FOREIGN PATENT DOCUMENTS

| WO | 2007-086695 | A1 | 8/2007 |
| WO | 2009-009756 | A2 | 1/2009 |

OTHER PUBLICATIONS

Li, Zhen, et al. Mechanism of Intrinsic Point Defects and Oxygen Diffusion in Yttrium Aluminum Garnet: First Principles Investigation. J. Am. Ceram. Soc. 95(11):3628-3633, 2012.

Ge, Z., Hayakawa, T., Ando, S., Ueda, M., Akiike, T., Miyamoto, H., Kajita, T. & Kakimoto, M.-A. (2008). Chem. Mater. 20,2532-2537.

Kido, J. S.-J. Su, H. Sasabe, T. Takeda, Pyridine-Containing Bipolar Host Materials for Highly Efficient Blue Phosphorescent OLEDs, Chem. Mater. 20(5), 1691-1693 (2008).

Chen, Chih-Hsin et al., Versatile, Benzimidazole/Amine-Based Ambipolar Compounds for Electroluminescent Applications: Single-Layer, Blue, Fluorescent OLEDs, Hosts for Single-Layer, Phosphorescent OLEDs. Advanced Functional Materials, 19(16):2661-2670, (2009).

Huang, Jinhai et al., Bipolar anthracene derivatives containing hole- and lectron-transporting moieties for highly efficient blue electroluminescence devices. Journal of Materials Chemistry 21(9): 2957-2964 (2011).

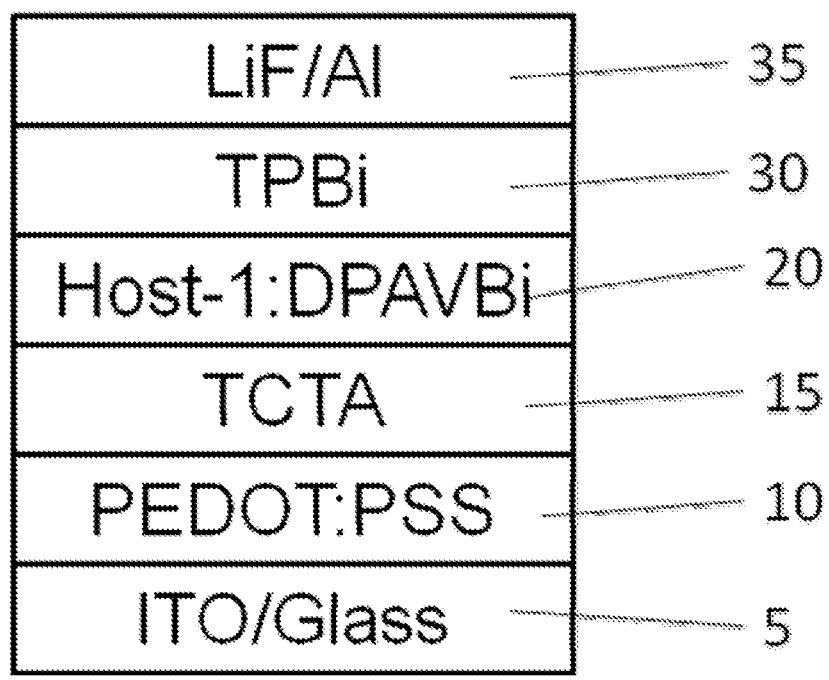

COMPOUNDS FOR USE IN LIGHT EMITTING DEVICES

CROSS REFERENCE TO RELATED APPLICATIONS

The present application claims the benefit under 35 U.S.C. 119(e) to U.S. Provisional Application Ser. No. 61/695,711 filed Aug. 31, 2012, the entire contents of which are hereby incorporated by reference in their entirety.

BACKGROUND

The embodiments disclosed herein include compounds for use in light-emitting devices.

Organic light-emitting devices (OLEDs) have been widely developed for flat panel displays, and the technology is quickly moving toward solid state lighting applications. The continued development of new host compounds to improve the efficiency and/or lifetimes of these devices can only help the devices realize their full commercial potential.

Host materials currently used in OLED devices can have problems with, for example, low stability, high charge injection barriers, imbalanced charge injection, and low charge mobilities, among other problems, all of which can result in low device efficiency and short lifetime. Therefore, there is a need for alternative host materials.

SUMMARY

Some embodiments include a host compound for use as in emissive elements of organic light emitting devices, the compound being represented by Formula 1:

HT-An-ET, wherein An is optionally substituted anthracenylene; HT is optionally substituted carbazolyl, optionally substituted carbazolylphenyl, optionally substituted phenylnaphthylamine, optionally substituted phenylnaphthylaminophenyl, optionally substituted diphenylaminophenyl or optionally substituted diphenylamine; and, ET is optionally substituted benzimidazol-2-yl, optionally substituted 3-(benzimidazol-2-yl)phenyl, optionally substituted benzothiazol-2-yl, optionally substituted 2-phenyl-benzothiazol, optionally substituted benzoxazol-2-yl, optionally substituted 3-(benzoxazol-2-yl)phenyl, optionally substituted 3,3'-bipyridin-5-yl, optionally substituted (3,3'-bipyridin-5-yl)phenyl, optionally substituted quinolin-8-yl, optionally substituted 3-(quinolin-8-yl)phenyl, optionally substituted quinolin-5-yl, optionally substituted (quinolin-5-yl)phenyl, optionally substituted quinoxalin-5-yl, or optionally substituted (quinoxalin-5-yl)phenyl.

Some embodiments include a host compound for use in emissive elements of organic light emitting devices, the compound being represented by Formula 2:

$HT^2$-$Ph^1$-An-$Ph^2$-$ET^2$, wherein An is optionally substituted anthracenylene; $Ph^1$ and $Ph^2$ are independently a bond or optionally substituted phenylene; $HT^2$ is optionally substituted carbazolyl, optionally substituted phenylnaphthylamine, or optionally substituted diphenylamine; and, $ET^2$ is an optionally substituted $C_{7-9}$ bicylic heteroaromatic ring system containing at least one ring nitrogen atom.

Some embodiments include a host compound for use in emissive elements of organic light emitting devices, the compound being represented by Formula 3:

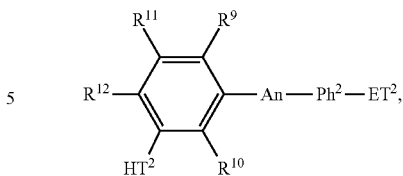

wherein An is optionally substituted anthracenylene; $Ph^2$ is a bond or optionally substituted phenylene; $HT^2$ is optionally substituted carbazolyl, optionally substituted phenylnaphthylamine, or optionally substituted diphenylamine; $ET^2$ is an optionally substituted $C_{7-9}$ bicylic heteroaromatic ring system containing at least one ring nitrogen atom; and, $R^9$, $R^{10}$, $R^{11}$, and $R^{12}$ are independently any substituents. In some embodiments, $R^9$ is H, $C_{1-3}$ alkyl, or $C_{1-3}$ perfluoroalkyl. In some embodiments, $R^{10}$ is H, $C_{1-3}$ alkyl, or $C_{1-3}$ perfluoroalkyl. In some embodiments, $R^{11}$ is H, $C_{1-3}$ alkyl, or $C_{1-3}$ perfluoroalkyl. In some embodiments, $R^{12}$ is H, $C_{1-3}$ alkyl, or $C_{1-3}$ perfluoroalkyl.

Some embodiments include a host compound for use in emissive elements of organic light emitting devices, the compound being represented by Formula 4:

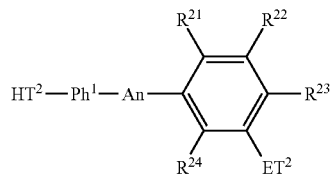

wherein An is optionally substituted anthracenylene; $Ph^1$ is a bond or optionally substituted phenylene; $HT^2$ is optionally substituted carbazolyl, optionally substituted phenylnaphthylamine, or optionally substituted diphenylamine; $ET^2$ is an optionally substituted $C_{7-9}$ bicylic heteroaromatic ring system containing at least one ring nitrogen atom; and, $R^{21}$, $R^{22}$, $R^{23}$, and $R^{24}$ are independently any substituents. In some embodiments, $R^{21}$ is H, $C_{1-3}$ alkyl, or $C_{1-3}$ perfluoroalkyl. In some embodiments, $R^{22}$ is H, $C_{1-3}$ alkyl, or $C_{1-3}$ perfluoroalkyl. In some embodiments, $R^{23}$ is H, $C_{1-3}$ alkyl, or $C_{1-3}$ perfluoroalkyl. In some embodiments, $R^{24}$ is H, $C_{1-3}$ alkyl, or $C_{1-3}$ perfluoroalkyl.

Some embodiments include a host compound for use in emissive elements of organic light emitting devices, the compound being represented by Formula 5:

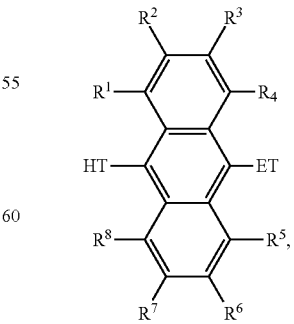

wherein $R^1$, $R^2$, $R^3$, $R^4$, $R^5$, $R^6$, $R^7$ and $R^8$ are independently any substituents; HT is optionally substituted carbazolyl, optionally substituted carbazolylphenyl, optionally substituted phenylnaphthylamine, optionally substituted phenylnaphthylaminophenyl, optionally substituted diphenylaminophenyl or optionally substituted diphenylamine; and, ET is optionally substituted benzimidazol-2-yl, optionally substituted 3-(benzimidazol-2-yl)phenyl, optionally substituted benzothiazol-2-yl, optionally substituted benzothiazol-2-yl)phenyl, (optionally substituted benzoxazol-2-yl, optionally substituted 3-(benzoxazol-2-yl)phenyl, optionally substituted 3,3'-bipyridin-5-yl, optionally substituted (3,3'-bipyridin-5-yl)phenyl, optionally substituted quinolin-8-yl, optionally substituted 3-(quinolin-8-yl)phenyl, optionally substituted quinolin-5-yl, optionally substituted (quinolin-5-yl)phenyl, optionally substituted quinoxalin-5-yl, or optionally substituted (quinoxalin-5-yl)phenyl. In some embodiments, $R^1$ is H, $C_{1-3}$ alkyl, or $C_{1-3}$ perfluoroalkyl. In some embodiments, $R^2$ is H, $C_{1-3}$ alkyl, or $C_{1-3}$ perfluoroalkyl. In some embodiments, $R^3$ is H, $C_{1-3}$ alkyl, or $C_{1-3}$ perfluoroalkyl. In some embodiments, $R^4$ is H, $C_{1-3}$ alkyl, or $C_{1-3}$ perfluoroalkyl. In some embodiments, $R^5$ is H, $C_{1-3}$ alkyl, or $C_{1-3}$ perfluoroalkyl. In some embodiments, $R^6$ is H, $C_{1-3}$ alkyl, or $C_{1-3}$ perfluoroalkyl. In some embodiments, $R^7$ is H, $C_{1-3}$ alkyl, or $C_{1-3}$ perfluoroalkyl. In some embodiments, $R^8$ is H, $C_{1-3}$ alkyl, or $C_{1-3}$ perfluoroalkyl. In some embodiments, $R^1$, $R^2$, $R^3$, $R^4$, $R^5$, $R^6$, $R^7$ and $R^8$ are independently H, $C_{1-3}$ alkyl, or $C_{1-3}$ perfluoroalkyl. In some embodiments, $R^1$, $R^2$, $R^3$, $R^4$, $R^5$, $R^6$, $R^7$ and $R^8$ are H.

Some embodiments include a host compound for use in emissive elements of organic light emitting devices, the compound being represented by Formula 6:

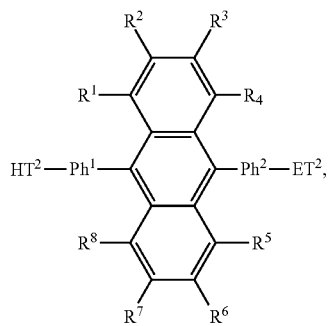

wherein $R^1$, $R^2$, $R^3$, $R^4$, $R^5$, $R^6$, $R^7$ and $R^8$ are independently any substituents; $Ph^1$ and $Ph^2$ are independently a bond or optionally substituted phenylene; $HT^2$ is optionally substituted carbazolyl, optionally substituted phenylnaphthylamine, or optionally substituted diphenylamine; and, $ET^2$ is an optionally substituted $C_{7-9}$ bicylic heteroaromatic ring system containing at least one ring nitrogen atom. In some embodiments, is H, $C_{1-3}$ alkyl, or $C_{1-3}$ perfluoroalkyl. In some embodiments, $R^1$ is H, $C_{1-3}$ alkyl, or $C_{1-3}$ perfluoroalkyl. In some embodiments, $R^2$ is H, $C_{1-3}$ alkyl, or $C_{1-3}$ perfluoroalkyl. In some embodiments, $R^3$ is H, $C_{1-3}$ alkyl, or $C_{1-3}$ perfluoroalkyl. In some embodiments, $R^4$ is H, $C_{1-3}$ alkyl, or $C_{1-3}$ perfluoroalkyl. In some embodiments, $R^5$ is H, $C_{1-3}$ alkyl, or $C_{1-3}$ perfluoroalkyl. In some embodiments, $R^7$ is H, $C_{1-3}$ alkyl, or $C_{1-3}$ perfluoroalkyl. In some embodiments, $R^8$ is H, $C_{1-3}$ alkyl, or $C_{1-3}$ perfluoroalkyl.

Some embodiments include a host compound for use in emissive elements of organic light emitting devices, the compound being:

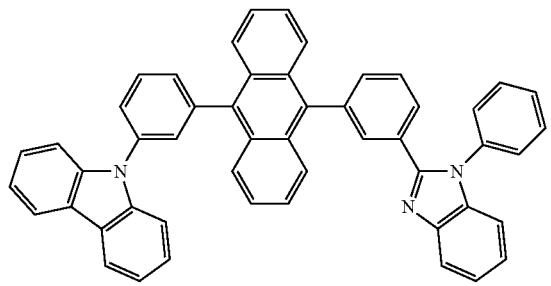 [SMILES: c1ccc(-n2c(-c3cccc(-c4c5ccccc5c(-c5cccc(-n6c7ccccc7c7ccccc76)c5)c5ccccc45)c3)nc3ccccc32)cc1]

9-(3-(10-(3-(1-phenyl-1H-benzo[d]imidazol-2-yl)phenyl)anthracen-9-yl)phenyl)-9H-carbazole
(Host-1)

Some embodiments include a host compound for use in emissive elements of organic light emitting devices, the compound being:

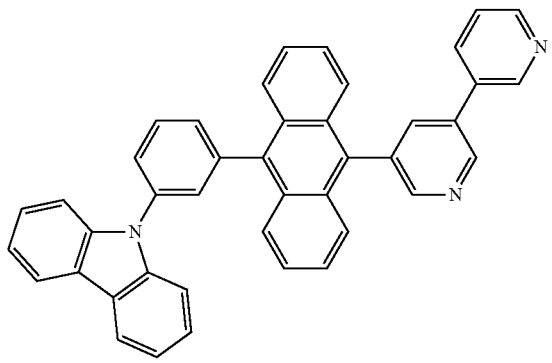 [SMILES: c1cncc(-c2cncc(-c3c4ccccc4c(-c4cccc(-n5c6ccccc6c6ccccc65)c4)c4ccccc34)c2)c1]

9-(3-(10-([3,3'-bipyridin]-5-yl)anthracen-9-yl)phenyl)-9H-carbazole (Host-2)

Some embodiments include an emissive layer comprising a compound of any of Formulas 1-26, optionally substituted 9-(3-(10-(3-(1-phenyl-1H-benzo[d]imidazol-2-yl)phenyl)anthracen-9-yl)phenyl)-9H-carbazole, or optionally substituted 9-(3-(10-([3,3'-bipyridin]-5-yl)anthracen-9-yl)phenyl)-9H-carbazole. Some embodiments provide a lighting device comprising the emissive layer described herein.

These and other embodiments are described in greater detail below.

BRIEF DESCRIPTION OF THE DRAWINGS

FIG. 1 is a schematic depiction of an embodiment of an organic light-emitting device.

DETAILED DESCRIPTION

By employing a newly designed molecular structure, one embodiment of which is demonstrated in an Example below, a new series of host materials is produced that can be used in OLED device applications. The synthesis of this series of host materials is straightforward and results in a high yield.

Unless otherwise indicated, when a compound or chemical structural feature such as aryl is referred to as being "optionally substituted," it includes a feature that has no substituents (i.e., unsubstituted), or a feature that is "substituted," meaning that the feature has one or more substituents. The term "substituent" has the broadest meaning known to one of ordinary skill in the art, and includes a moiety that replaces one or more hydrogen atoms attached to a parent compound or structural feature. In some embodiments, a substituent may be an ordinary organic moiety known in the art, which may have a molecular weight (e.g., the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, Si, F, Cl, Br, or I; provided that the substituent includes one C, N, O, S, Si, F, Cl, Br, or I atom. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, etc.

For convenience, the term "molecular weight" is used with respect to a moiety or part of a molecule to indicate the sum of the atomic masses of the atoms in the moiety or part of a molecule, even though it may not be a complete molecule.

The structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by -|, attachment may occur at any position normally occupied by a hydrogen atom.

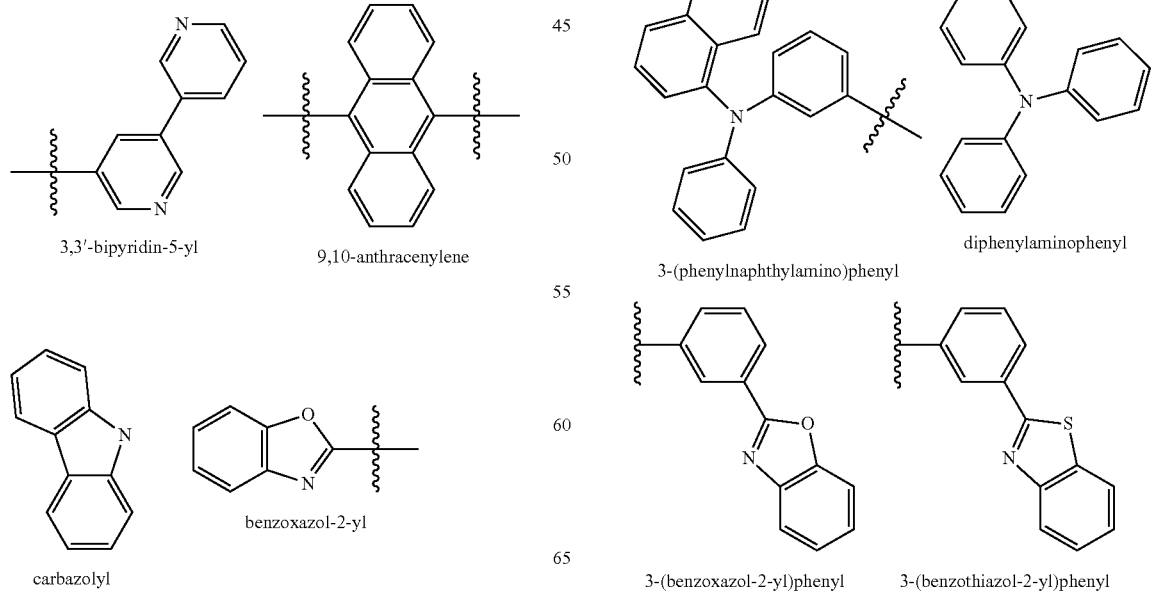

-continued

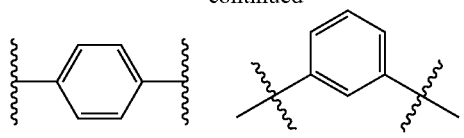

1,4-interphenylene m-phenylene or
1,3-interphenylene

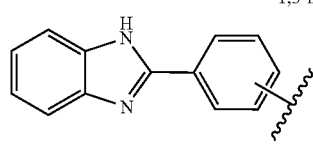

(benzimidazol-2-yl)phenyl

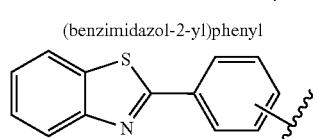

(benzothiazol-2-yl)phenyl

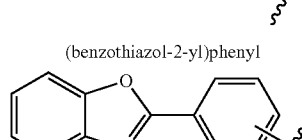

(benzoxazol-2-yl)phenyl

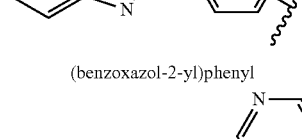

(3,3'-bipyridin-5-yl)phenyl

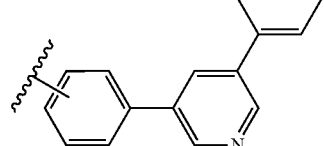

(quinolin-8-yl)phenyl    (quinolin-5-yl)phenyl

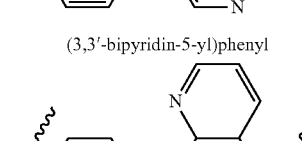

(quinoxalin-5-yl)phenyl

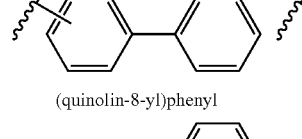

3-(benzimidazol-2-yl)phenyl

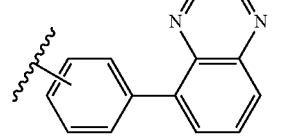

3-(benzothiazol-2-yl)phenyl

-continued

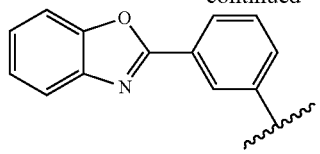

3-(benzoxazol-2-yl)phenyl

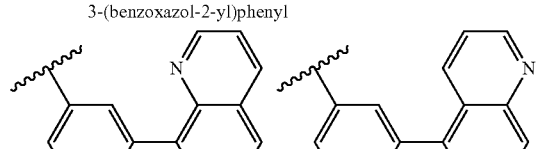

3-(quinolin-8-yl)phenyl    3-(quinolin-5-yl)phenyl

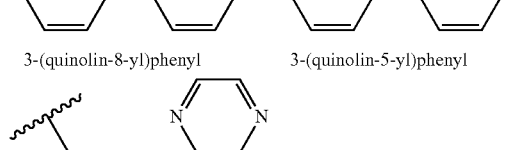

3-(quinoxalin-5-yl)phenyl

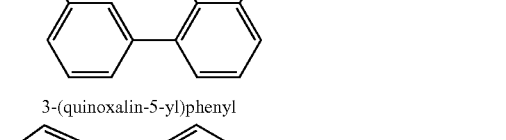

3-(carbazolyl)phenyl

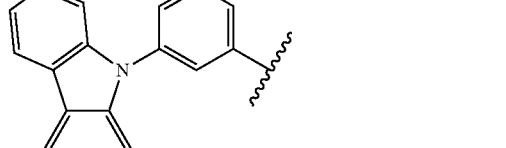

3-(diphenylamino)phenyl phenylnaphthylaminophenyl

Some embodiments herein comprise optionally substituted 9-(3-(10-(3-(1-phenyl-1H-benzo[d]imidazol-2-yl)phenyl)anthracen-9-yl)phenyl)-9H-carbazole (Host-1). Some embodiments herein comprise optionally substituted 9-(3-(10-([3,3'-bipyridin]-5-yl)anthracen-9-yl)phenyl)-9H-carbazole (Host-2).

As used herein, the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—CH$_3$), ethyl (—CH$_2$CH$_3$), n-propyl (—CH$_2$CH$_2$CH$_3$), n-butyl (—CH$_2$CH$_2$CH$_2$CH$_3$), n-pentyl (—CH$_2$CH$_2$CH$_2$CH$_2$CH$_3$), n-hexyl (—CH$_2$CH$_2$CH$_2$CH$_2$CH$_2$CH$_3$), etc.; $C_{3-10}$ branched alkyl, such as C$_3$H$_7$ (e.g., iso-propyl), C$_4$H$_9$ (e.g., branched butyl isomers), C$_5$H$_{11}$ (e.g., branched pentyl isomers), C$_6$H$_{13}$ (e.g., branched hexyl isomers), C$_7$H$_{15}$ (e.g., heptyl isomers), etc.; $C_{3-10}$ cycloalkyl, such as C$_3$H$_5$ (e.g., cyclopropyl), C$_4$H$_7$ (e.g., cyclobutyl isomers such as cyclobutyl, methylcyclopropyl, etc.), $C_5H_9$ (e.g., cyclopentyl isomers such as cyclopentyl, methylcyclobutyl, dimethylcyclopropyl, etc.), $C_6H_{11}$ (e.g., cyclohexyl isomers), $C_7H_{13}$ (e.g., cycloheptyl isomers), etc.; and the like.

With respect to an optionally substituted moiety such as optionally substituted alkyl, a phrase such as "optionally substituted $C_{1-12}$ alkyl" refers to a $C_{1-12}$ alkyl that may be unsubstituted, or may have 1 or more substituents, and does not limit the number of carbon atoms in any substituent. A phrase such as "$C_{1-12}$ optionally substituted alkyl" refers to unsubstituted $C_{1-12}$ alkyl, or substituted alkyl wherein both the alkyl parent and all substituents have from 1-12 carbon atoms. Similar conventions may be applied to other optionally substituted moieties such as aryl and heteroaryl.

Substituents on alkyl may be the same as those described generally above, except that alkyl may not have an alkyl substituent. In some embodiments, substituents on alkyl are independently selected from F, Cl, Br, I, CN, $CO_2H$, —O-alkyl, ester groups, acyl, amine groups, and amide groups, and may have a molecular weight of about 15 to about 100 or about 500.

The term "perfluoroalkyl" refers to fluoroalkyl with a formula $C_nF_{2n+1}$ for a linear or branched structure. Perfluoroalkyl can be, for example: $CF_3$, $C_2F_5$, $C_3F_7$, $C_4F_9$, $C_5F_{11}$, $C_6F_{13}$, etc.; or, $C_nF_{2n}$ for a cyclic structure, e.g. cyclic $C_3F_6$, cyclic $C_4F_8$, cyclic $C_5F_{10}$, cyclic $C_6F_{12}$, etc. In other words, every hydrogen atom in the alkyl is replaced by fluorine. For example, $C_{1-3}$ perfluoroalkyl refers to $CF_3$, $C_2F_5$, and $C_3F_7$ isomers.

As used herein the term "aryl" has the broadest meaning generally understood in the art, and may include an aromatic ring or aromatic ring system such as phenyl, naphthyl, etc. The term "heteroaryl" also has the meaning understood by a person of ordinary skill in the art, and includes an "aryl" which has one or more heteroatoms in the ring or ring system, such as pyridinyl, furyl, thienyl, oxazolyl, thiazolyl, imidazolyl, indolyl, quinolinyl, benzofuranyl, benzothienyl, benzoxazolyl, benzothiazolyl, benzimidazolyl, etc.

If stereochemistry is not indicated, a name or structural depiction includes any stereoisomer or any mixture of stereoisomers.

With respect to any relevant formula or structural depiction herein, HT can be optionally substituted carbazolyl, optionally substituted carbazolylphenyl, optionally substituted phenylnaphthylamine, optionally substituted phenylnaphthylaminophenyl, optionally substituted diphenylaminophenyl, or optionally substituted diphenylamine.

In some embodiments HT may be optionally substituted. If HT is substituted, it may have 1, 2, 3, 4, or 5 substituents. Any substituent may be included on HT. In some embodiments, some or all of the substituents on HT may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may independently be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, HT is unsubstituted.

With respect to any relevant formula or structural depiction herein, ET can be an optionally substituted $C_{7-9}$ bicyclic heteroaromatic ring system containing at least one ring nitrogen atom. In some embodiments, ET has one nitrogen atom, and in some embodiments ET has two nitrogen atoms. In some embodiments, ET can be optionally substituted benzimidazol-2-yl, optionally substituted 3-(benzimidazol-2-yl)phenyl, optionally substituted benzothiazol-2-yl, optionally substituted 3-(benzothiazol-2-yl)phenyl, optionally substituted benzoxazol-2-yl, optionally substituted 3-(benzoxazol-2-yl)phenyl, optionally substituted 3,3'-bipyridin-5-yl, optionally substituted (3,3'-bipyridin-5-yl)phenyl, optionally substituted quinolin-8-yl, optionally substituted 3-(quinolin-8-yl)phenyl, optionally substituted quinolin-5-yl, optionally substituted (quinolin-5-yl)phenyl, optionally substituted quinoxalin-5-yl, or optionally substituted (quinoxalin-5-yl)phenyl.

In some embodiments ET may be optionally substituted. If ET is substituted, it may have 1, 2, 3, 4, or 5 substituents. Any substituent may be included on ET. In some embodiments, some or all of the substituents on ET may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may independently be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, ET is unsubstituted.

With respect to any relevant formula or structural depiction herein, $HT^2$ can be optionally substituted carbazolyl, optionally substituted phenylnaphthylamine, or optionally substituted diphenylamine.

In some embodiments $HT^2$ may be optionally substituted. If $HT^2$ is substituted, it may have 1, 2, 3, 4, or 5 substituents. Any substituent may be included on $HT^2$. In some embodiments, some or all of the substituents on $HT^2$ may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may independently be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, $HT^2$ is unsubstituted.

With respect to any relevant formula or structural depiction herein, such as Formula 2, $ET^2$ can be an optionally substituted $C_{7-9}$ bicyclic heteroaromatic ring system containing at least one ring nitrogen atom. In some embodiments $ET^2$ has one N, and in some embodiments $ET^2$ has two N. In some embodiments $ET^2$ is optionally substituted benzimidazol-2-yl, optionally substituted benzothiazol-2-yl, optionally substituted benzoxazol-2-yl, optionally substituted 3,3'-bipyridin-5-yl, optionally substituted quinolin-8-yl, optionally substituted quinolin-5-yl, or optionally substituted quinoxalin-5-yl.

In some embodiments $ET^2$ may be optionally substituted. If $ET^2$ is substituted, it may have 1, 2, 3, 4, or 5 substituents. Any substituent may be included on $ET^2$. In some embodiments, some or all of the substituents on $ET^2$ may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may independently be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as $-O_2CCH_3$, $-CO_2CH_3$, $-O_2CC_2H_5$, $-CO_2C_2H_5$, $-O_2C$-phenyl, $-CO_2$-phenyl, etc.; a $C_{1-10}$ ketone such as $-COCH_3$, $-COC_2H_5$, $-COC_3H_7$, $-CO$-phenyl, etc.; or a $C_{1-10}$ amine such as $NH_2$, $NH(CH_3)$, $N(CH_3)_2$, $N(CH_3)C_2H_5$, etc. In some embodiments, $ET^2$ is unsubstituted.

In some embodiments, HT can be:

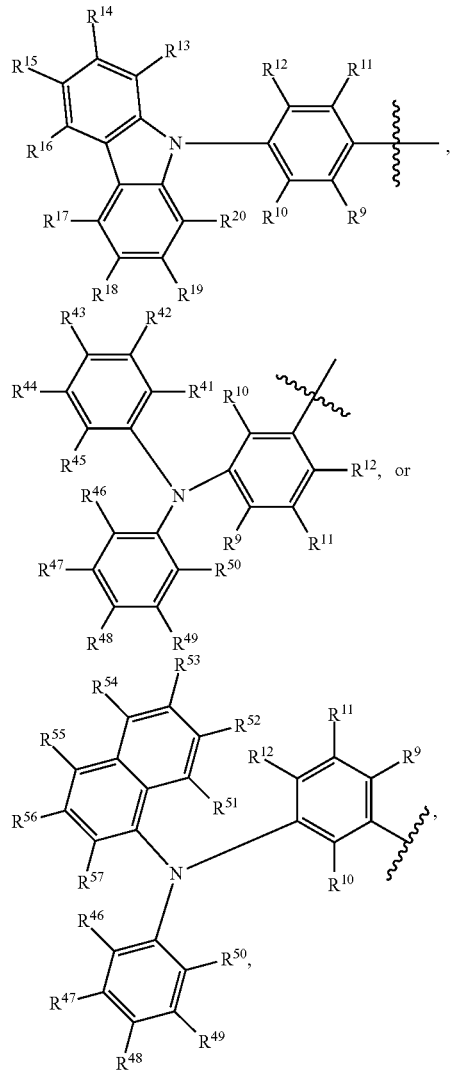

wherein $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, and $R^{57}$ are independently any substituents. In some embodiments, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, and $R^{57}$ are H, $C_{1-3}$ alkyl, or $C_{1-3}$ perfluoroalkyl.

In some embodiments, ET can be:

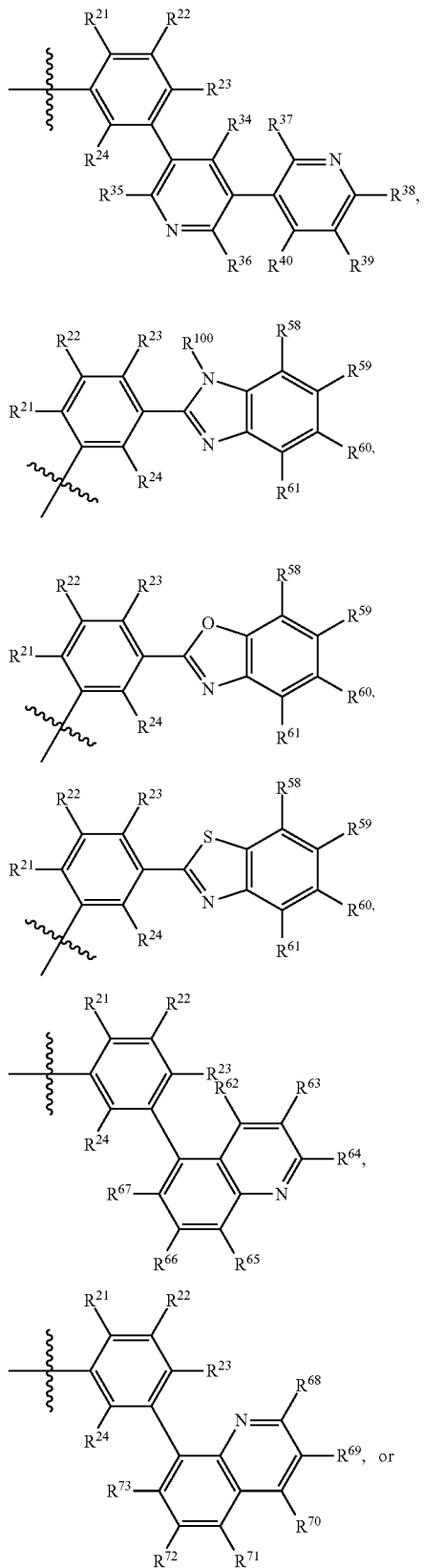

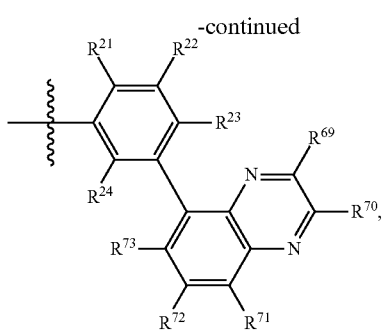

wherein $R^{21}$, $R^{22}$, $R^{23}$, $R^{24}$, $R^{34}$, $R^{35}$, $R^{36}$, $R^{37}$, $R^{38}$, $R^{39}$, $R^{40}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, and $R^{100}$ are independently any substituents. In some embodiments, $R^{21}$, $R^{22}$, $R^{23}$, $R^{24}$, $R^{34}$, $R^{35}$, $R^{36}$, $R^{37}$, $R^{38}$, $R^{39}$, $R^{40}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, and $R^{73}$ are independently H, $C_{1-3}$ alkyl, or $C_{1-3}$ perfluoroalkyl; and $R^{100}$ is H, $C_{1-3}$ alkyl, $C_{1-3}$ perfluoroalkyl, or optionally substituted phenyl.

In some embodiments, $HT^2$ can be:

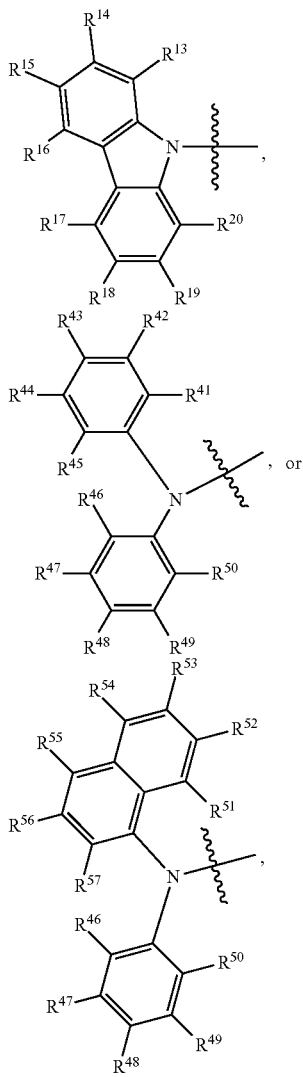

wherein $R^{13}$, $R^{14}$, $R^{15}$, $R^{16}$, $R^{17}$, $R^{18}$, $R^{19}$, $R^{20}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, and $R^{57}$ are independently any substituents. In some embodiments, $R^{13}$, $R^{14}$, $R^{15}$, $R^{16}$, $R^{17}$, $R^{18}$, $R^{19}$, $R^{20}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, and $R^{57}$ are independently H, $C_{1-3}$ alkyl, or $C_{1-3}$ perfluoroalkyl.

In some embodiments, $ET^2$ can be:

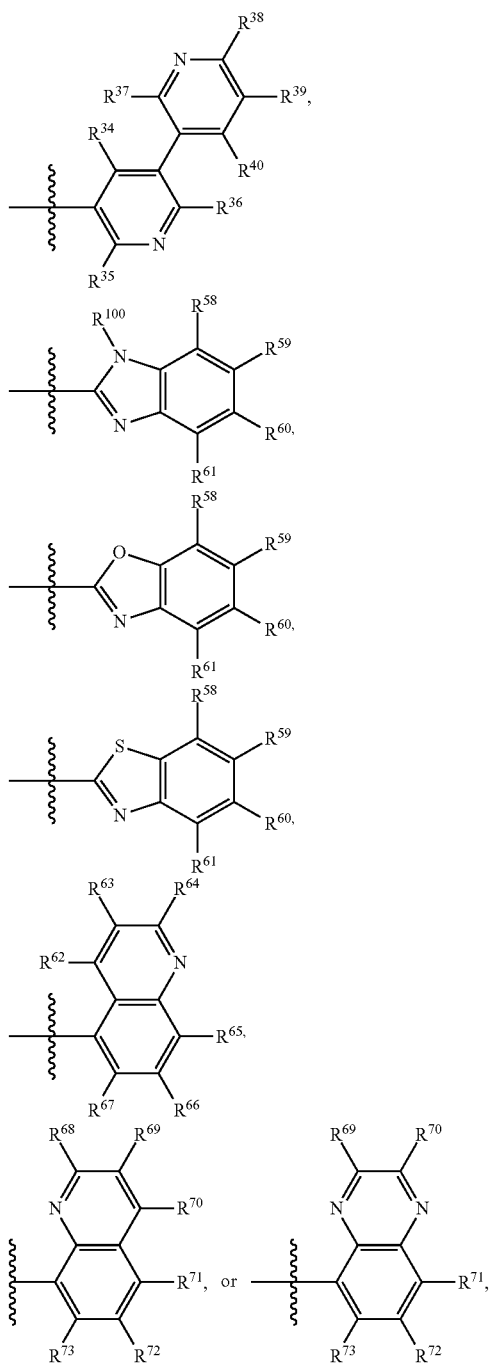

wherein $R^{34}$, $R^{35}$, $R^{36}$, $R^{37}$, $R^{38}$, $R^{39}$, $R^{40}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, and $R^{100}$ are independently any substituents. In some embodiments, wherein $R^{34}$, $R^{35}$, $R^{36}$, $R^{37}$, $R^{38}$, $R^{39}$, $R^{40}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, and $R^{73}$ are independently H, $C_{1-3}$ alkyl, or $C_{1-3}$ perfluoroalkyl; and $R^{100}$ is H, $C_{1-3}$ alkyl, $C_{1-3}$ perfluoroalkyl, or optionally substituted phenyl.

Some embodiments can include a compound represented by one or more of Formulas 5-26, as follows:
Formula 5
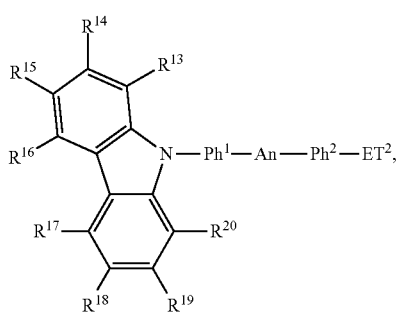
Formula 6
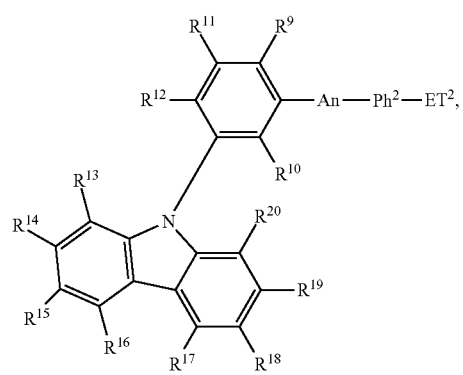
Formula 7
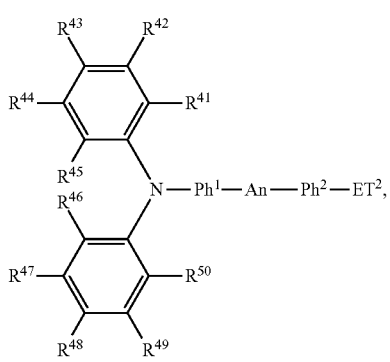
Formula 8
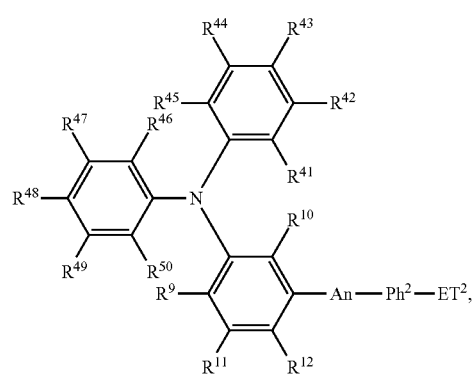
Formula 9
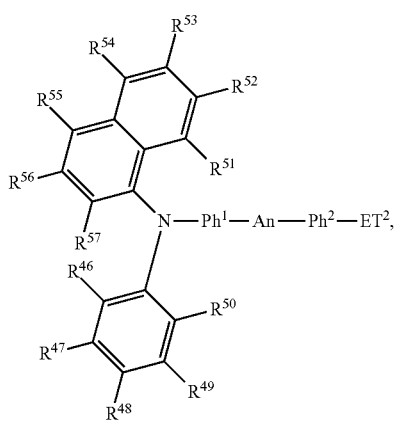
Formula 10
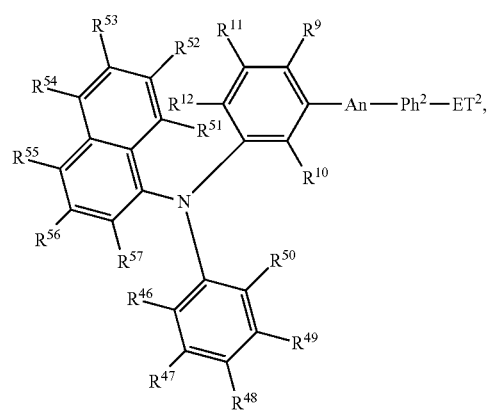
Formula 11
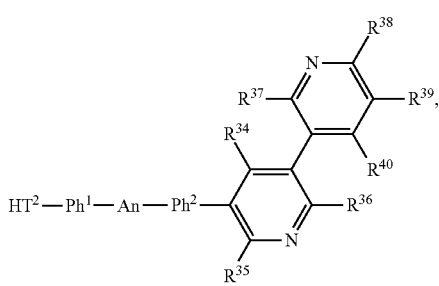
Formula 12
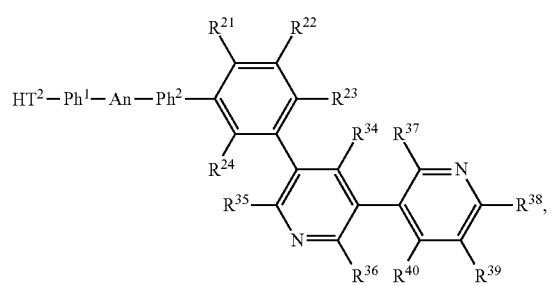

Formula 13
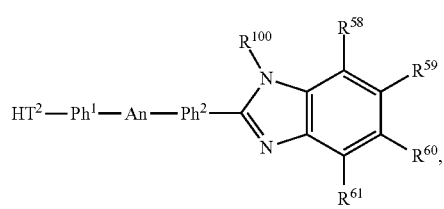
Formula 14
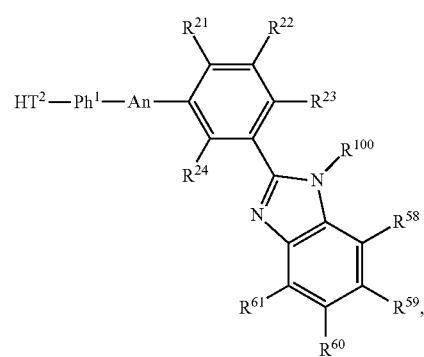
Formula 15
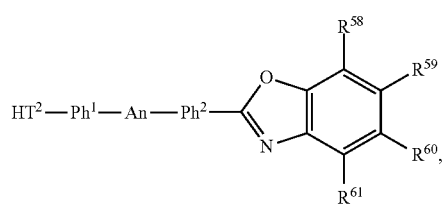
Formula 16
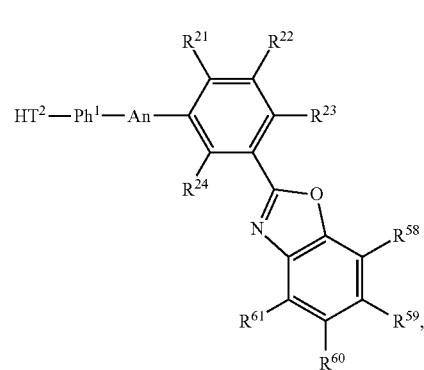
Formula 17
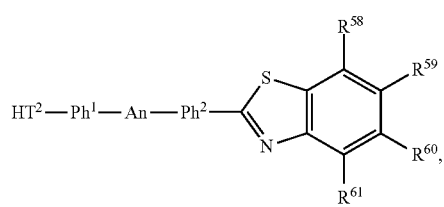
Formula 18
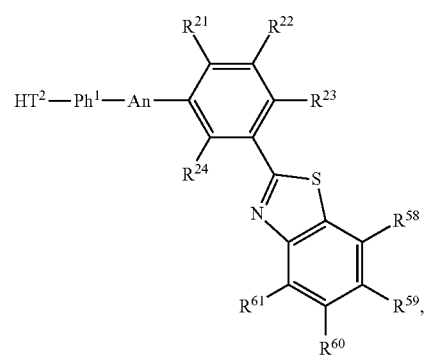
Formula 19
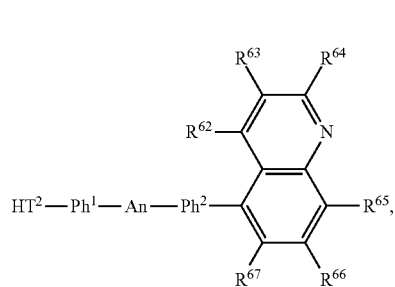
Formula 20
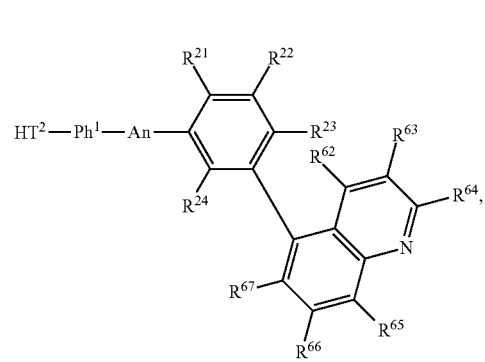

-continued
Formula 21
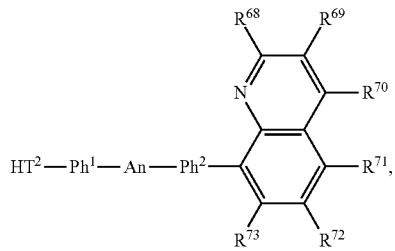
Formula 22
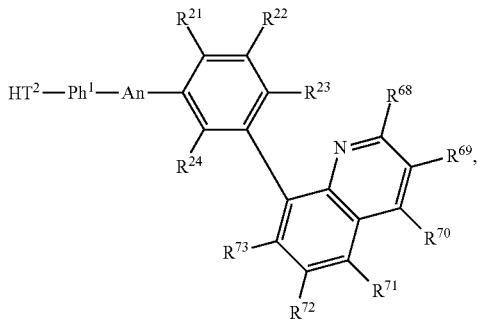
Formula 23
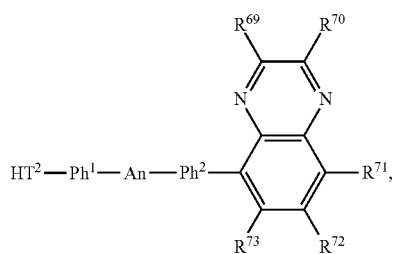
Formula 24
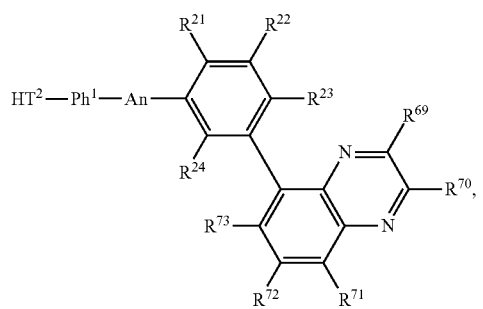
Formula 25
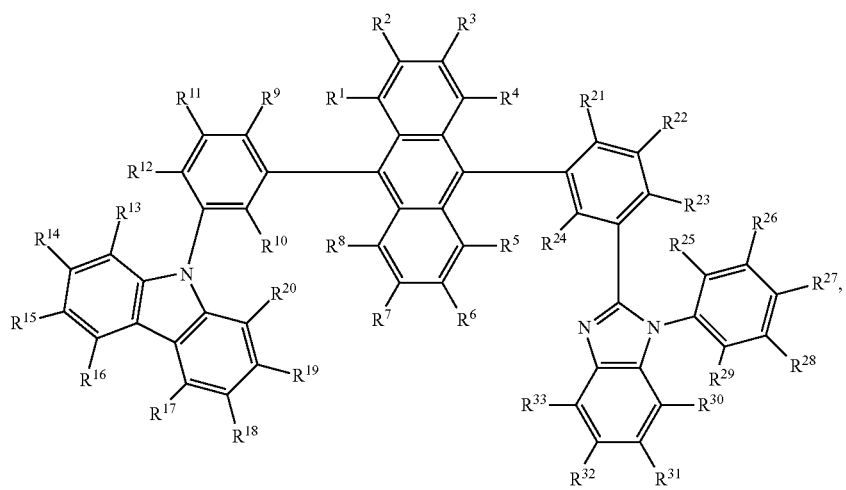
Formula 26
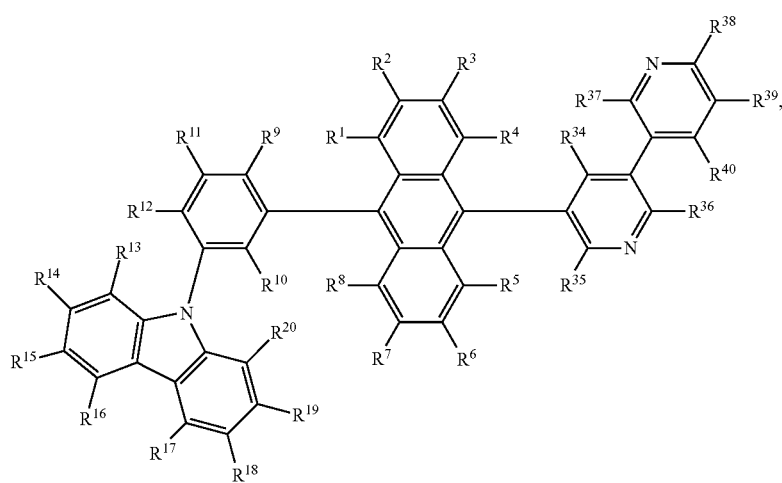

HT²—Ph¹—An—ET²,                                          Formula 27

Formula 28

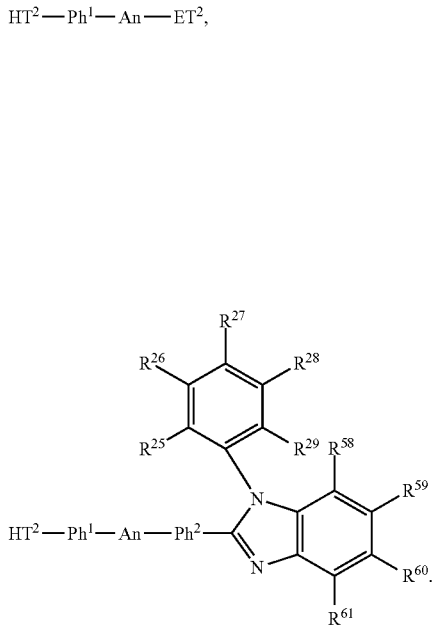

, and

Formula 29

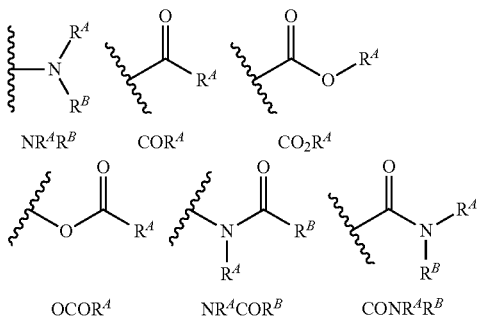

Generally $R^1$-$R^{73}$ and $R^{100}$ can be H or any substituent, such as a substituent having from 0 to 6 carbon atoms and from 0 to 5 heteroatoms, wherein each heteroatom is independently: O, N, S, F, Cl, Br, or I, and/or having a molecular weight of 15 g/mol to 300 g/mol. Any of $R^1$-$R^{73}$ and $R^{100}$ may comprise: a) 1 or more alkyl moieties optionally substituted with, or optionally connected by or to, b) 1 or more functional groups, such as C=C, C≡C, CO, $CO_2$, CON, $NCO_2$, OH, SH, O, S, N, N=C, F, Cl, Br, I, CN, $NO_2$, $CO_2H$, $NH_2$, etc.; or, may be a substituent having no alkyl portion, such as F, Cl, Br, I, $NO_2$, CN, $NH_2$, OH, COH, $CO_2H$, etc. In some embodiments $R^1$-$R^{73}$ and $R^{100}$ are independently H, $C_{1-3}$ alkyl, or $C_{1-3}$ perfluoroalkyl.

With respect to any relevant formula or structural depiction herein, some non-limiting examples of $R^1$ may include $R^A$, F, CN, $OR^A$, $CF_3$, $NO_2$, $NR^A R^B$, $COR^A$, $CO_2 R^A$, $OCOR^A N$-$R^A COR^B$, $CONR^A R^B$, etc. In some embodiments, $R^1$ may be H; $C_{1-3}$ alkyl, such as methyl, ethyl, propyl isomers (e.g., n-propyl and isopropyl), cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^1$ may be H.

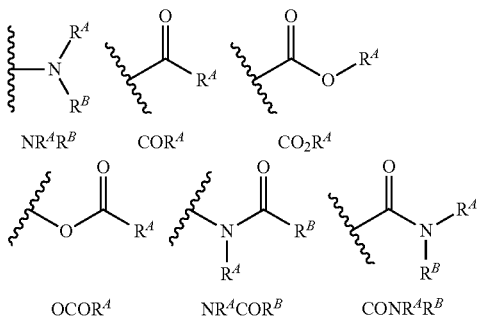

Each $R^A$ may independently be H, or $C_{1-12}$ alkyl, including: linear or branched alkyl having a formula $C_a H_{a+1}$, or cycloalkyl having a formula $C_a H_{a-1}$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^A$ may be H or $C_{1-6}$ alkyl. In some embodiments, $R^A$ may be H or $C_{1-3}$ alkyl. In some embodiments, $R^A$ may be H or $CH_3$. In some embodiments, $R^A$ may be H.

Each $R^B$ may independently be H, or $C_{1-12}$ alkyl, including: linear or branched alkyl having a formula $C_a H_{a+1}$, or cycloalkyl having a formula $C_a H_a$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_8H_{17}$, $C_7H_{15}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^B$ may be H or $C_{1-3}$ alkyl. In some embodiments, $R^B$ may be H or $CH_3$. In some embodiments, $R^B$ may be H.

With respect to any relevant formula or structural depiction herein, some non-limiting examples of $R^2$ may include $R^A$, F, Cl, $OR^A$, $CF_3$, $NO_2$, $NR^A R^B$, $COR^A$, $CO_2 R^A$, $OCOR^A N$-$R^A COR^B$, $CONR^A R^B$, etc. In some embodiments, $R^2$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^2$ may be H.

With respect to any relevant formula or structural depiction herein, some non-limiting examples of $R^3$ may include $R^A$, F, Cl, CN, $CF_3$, $NO_2$, $NR^A R^B$, $COR^A$, $CO_2 R^A$, $OCOR^A N$-$R^A COR^B$, $CONR^A R^B$, etc. In some embodiments, $R^3$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^3$ may be H.

With respect to any relevant formula or structural depiction herein, some non-limiting examples of $R^4$ may include $R^A$, F, Cl, CN, $OR^A$, $CF_3$, $NO_2$, $COR^A$, $CO_2 R^A$, $OCOR^A NR^A COR^B$, $CONR^A R^B$, etc. In some embodiments, $R^4$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^4$ may be H.

With respect to any relevant formula or structural depiction herein, some non-limiting examples of $R^5$ may include $R^A$, F, $CF_3$, $NO_2$, $NR^AR^B$, $COR^A$, $CO_2R^A$, $OCOR^A$ $NR^ACOR^B$, $CONR^AR^B$, etc. In some embodiments, $R^5$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^5$ may be H.

With respect to any relevant formula or structural depiction herein, some non-limiting examples of $R^6$ may include $R^A$, F, Cl, CN, $OR^A$, $CF_3$, $COR^A$, $CO_2R^A$, $OCOR^A$ $NR^ACOR^B$, $CONR^AR^B$, etc. In some embodiments, $R^6$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^6$ may be H.

With respect to any relevant formula or structural depiction herein, some non-limiting examples of $R^7$ may include $R^A$, F, Cl, CN, $OR^A$, $CF_3$, $NR^AR^B$, $COR^A$, $CO_2R^A$, $OCOR^AN$-$R^ACOR^B$, $CONR^AR^B$, etc. In some embodiments, $R^7$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^7$ may be H.

With respect to any relevant formula or structural depiction herein, some non-limiting examples of $R^8$ may include $R^A$, F, $CF_3$, $OCOR^A$, etc. In some embodiments, $R^8$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^8$ may be H.

With respect to any relevant formula or structural depiction herein, some non-limiting examples of $R^9$ may include $R^A$, F, $OR^A$, $CF_3$, $NO_2$, $NR^AR^B$, $COR^A$, $CO_2R^A$, $OCOR^AN$-$R^ACOR^B$, $CONR^AR^B$, etc. In some embodiments, $R^9$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^9$ may be H.

With respect to any relevant formula or structural depiction herein, some non-limiting examples of $R^{10}$ may include $R^A$, F, $CF_3$, etc. In some embodiments, $R^{10}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{10}$ may be H.

With respect to any relevant formula or structural depiction herein, some non-limiting examples of $R^{11}$ may include $R^A$, F, CN, $OR^A$, $CF_3$, $NO_2$, $NR^ACOR^B$, $CONR^AR^B$, etc. In some embodiments, $R^{11}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{11}$ may be H.

With respect to any relevant formula or structural depiction herein, some non-limiting examples of $R^{12}$ may include $R^A$, F, $CF_3$, $NR^AR^B$, $COR^A$, $CO_2R^A$, $OCOR^A$ $NR^ACOR^B$, $CONR^AR^B$, etc. In some embodiments, $R^{12}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{12}$ may be H.

With respect to any relevant formula or structural depiction herein, some non-limiting examples of $R^{13}$ may include $R^A$, F, Cl, $CF_3$, $NO_2$, $COR^A$, $CO_2R^A$, $OCOR^A$ etc. In some embodiments, $R^{13}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{13}$ may be H.

With respect to any relevant formula or structural depiction herein, some non-limiting examples of $R^{14}$ may include $R^A$, F, Cl, CN, $OR^A$, $CF_3$, $NO_2$, $NR^AR^B$, $COR^A$, $CO_2R^A$, $OCOR^AN$-$R^ACOR^B$, $CONR^AR^B$, etc. In some embodiments, $R^{14}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{14}$ may be H.

With respect to any relevant formula or structural depiction herein, some non-limiting examples of $R^{15}$ may include $R^A$, F, CN, $OR^A$, $CF_3$, $NO_2$, $NR^AR^B$, $COR^A$, $CO_2R^A$, $OCOR^AN$-$R^ACOR^B$, etc. In some embodiments, $R^{15}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{15}$ may be H.

With respect to any relevant formula or structural depiction herein, some non-limiting examples of $R^{16}$ may include $R^A$, F, Cl, CN, $CF_3$, $NR^AR^B$, $COR^A$, $CO_2R^A$, $OCOR^A$ $NR^ACOR^B$, $CONR^AR^B$, etc. In some embodiments, $R^{16}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{16}$ may be H.

With respect to any relevant formula or structural depiction herein, some non-limiting examples of $R^{17}$ may include $R^A$, F, CN, $OR^A$, $CF_3$, $NO_2$, $NR^AR^B$, $COR^A$, $CO_2R^A$, $OCOR^AN$-$R^ACOR^B$, $CONR^AR^B$, etc. In some embodiments, $R^{17}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{17}$ may be H.

With respect to any relevant formula or structural depiction herein, some non-limiting examples of $R^{18}$ may include $R^A$, F, Cl, CN, $CF_3$, $NO_2$, $NR^AR^B$, $COR^A$, $CO_2R^A$, $OCOR^AN$-$R^ACOR^B$, $CONR^AR^B$, etc. In some embodiments, $R^{18}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{18}$ may be H.

With respect to any relevant formula or structural depiction herein, some non-limiting examples of $R^{19}$ may include $R^A$, F, Cl, CN, $OR^A$, $CF_3$, $NO_2$, $CO_2R^A$, $OCOR^A$ $NR^ACOR^B$, $CONR^AR^B$, etc. In some embodiments, $R^{19}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{19}$ may be H.

With respect to any relevant formula or structural depiction herein, some non-limiting examples of $R^{20}$ may include $R^A$, F, Cl, CN, $OR^A$, $CF_3$, $NO_2$, $NR^AR^B$, $CO_2R^A$, $OCOR^AN$-$R^ACOR^B$, $CONR^AR^B$, etc. In some embodiments, $R^{20}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{20}$ may be H.

With respect to any relevant formula or structural depiction herein, some non-limiting examples of $R^{21}$ may include $R^A$, F, Cl, CN, $OR^A$, $CF_3$, $NO_2$, $NR^AR^B$, $COR^A$, $CO_2R^A$, $OCOR^AN$-

$R^A COR^B$, etc. In some embodiments, $R^{21}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{21}$ may be H.

With respect to any relevant formula or structural depiction herein, some non-limiting examples of $R^{22}$ may include $R^A$, F, Cl, CN, $OR^A$, $CF_3$, $NO_2$, $NR^A R^B$, $COR^A$, $CO_2 R^A$, $CONR^A R^B$, etc. In some embodiments, $R^{22}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{22}$ may be H.

With respect to any relevant formula or structural depiction herein, some non-limiting examples of $R^{23}$ may include $R^A$, F, Cl, CN, $OR^A$, $CF_3$, $NO_2$, $NR^A R^B$, $COR^A$, $CO_2 R^A$, $NR^A COR^B$, $CONR^A R^B$, etc. In some embodiments, $R^{23}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{23}$ may be H.

With respect to any relevant formula or structural depiction herein, some non-limiting examples of $R^{24}$ may include $R^A$, F, Cl, CN, $OR^A$, $CF_3$, $NO_2$, $NR^A R^B$, $COR^A$, $CO_2 R^A$, $NR^A COR^B$, etc. In some embodiments, $R^{24}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{24}$ may be H.

With respect to any relevant formula or structural depiction herein, some non-limiting examples of $R^{25}$ may include $R^A$, F, $CF_3$, $NO_2$, $NR^A R^B$, $COR^A$, $CO_2 R^A$, $NR^A COR^B$, $CONR^A R^B$, etc. In some embodiments, $R^{25}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{25}$ may be H.

With respect to any relevant formula or structural depiction herein, some non-limiting examples of $R^{26}$ may include $R^A$, F $CF_3$, etc. In some embodiments, $R^{26}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{26}$ may be H.

With respect to any relevant formula or structural depiction herein, some non-limiting examples of $R^{27}$ may include $R^A$, F, $CF_3$, etc. In some embodiments, $R^{27}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{27}$ may be H.

With respect to any relevant formula or structural depiction herein, some non-limiting examples of $R^{28}$ may include $R^A$, $FCF_3$, $COR^A$, $CO_2 R^A$, $NR^A COR^B$, $CONR^A R^B$, etc. In some embodiments, $R^{28}$ may be H; $C_{1-3}$ alkyl, such as methyl, ethyl, propyl isomers, cyclopropyl; or $C_{1-3}$ perfluoroalkyl, such as perfluoromethyl, perfluoroethyl, perfluoropropyl isomers, perfluorocyclopropyl, etc. In some embodiments, $R^{28}$ may be H.

With respect to any relevant formula or structural depiction herein, some non-limiting examples of $R^{29}$ may include $R^A$, F, CN, $OR^A$, $CF_3$, $NO_2$, $NR^A R^B$, $COR^A$, $CO_2 R^A$, $NR^A COR^B$, $CONR^A R^B$, etc. In some embodiments, $R^{29}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{29}$ may be H.

With respect to any relevant formula or structural depiction herein, some non-limiting examples of $R^{30}$ may include $R^A$, F, CN, $OR^A$, $CF_3$, $NO_2$, $COR^A$, $CO_2 R^A$, $NR^A COR^B$, $CONR^A R^B$, etc. In some embodiments, $R^{30}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{30}$ may be H.

With respect to any relevant formula or structural depiction herein, some non-limiting examples of $R^{31}$ may include $R^A$, F, Cl, $OR^A$, $CF_3$, $NO_2$, $COR^A$, $CO_2 R^A$, $NR^A COR^B$, $CONR^A R^B$, etc. In some embodiments, $R^{31}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{31}$ may be H.

With respect to any relevant formula or structural depiction herein, some non-limiting examples of $R^{32}$ may include $R^A$, F, Cl, CN, $OR^A$, $CF_3$, $NR^A R^B$, $CO_2 R^A$, $NR^A COR^B$, $CONR^A R^B$, etc. In some embodiments, $R^{32}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{32}$ may be H.

With respect to any relevant formula or structural depiction herein, some non-limiting examples of $R^{33}$ may include $R^A$, F, Cl, CN, $OR^A$, $CF_3$, $NO_2$, $NR^A R^B$, $COR^A$, $CO_2 R^A$, etc. In some embodiments, $R^{33}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{33}$ may be H.

With respect to any relevant formula or structural depiction herein, some non-limiting examples of $R^{34}$ may include $R^A$, F, $CF_3$, etc. In some embodiments, $R^{34}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{34}$ may be H.

With respect to any relevant formula or structural depiction herein, some non-limiting examples of $R^{35}$ may include $R^A$, F, $CF_3$, etc. In some embodiments, $R^{35}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{35}$ may be H.

With respect to any relevant formula or structural depiction herein, some non-limiting examples of $R^{36}$ may include $R^A$, F, Cl, CN, $OR^A$, $CF_3$, $NO_2$, $NR^A R^B$, $COR^A$, $CO_2 R^A$, etc. In some embodiments, $R^{36}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{36}$ may be H.

With respect to any relevant formula or structural depiction herein, some non-limiting examples of $R^{37}$ may include $R^A$, F, $CF_3$, $NO_2$, $NR^A R^B$, $COR^A$, $CO_2 R^A$, $NR^A COR^B$, $CONR^A R^B$, etc. In some embodiments, $R^{37}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{37}$ may be H.

With respect to any relevant formula or structural depiction herein, some non-limiting examples of $R^{38}$ may include $R^A$, F, Cl, ON, $OR^A$, $CF_3$, $NO_2$, $NR^A R^B$, $COR^A$, $CO_2 R^A$, $NR^A COR^B$, $CONR^A R^B$, etc. In some embodiments, $R^{38}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{38}$ may be H.

With respect to any relevant formula or structural depiction herein, some non-limiting examples of $R^{39}$ may include $R^A$, F, Cl, ON, $OR^A$, $CF_3$, $CO_2R^A$, $NR^ACOR^B$, $CONR^AR^B$, etc. In some embodiments, $R^{39}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{39}$ may be H.

With respect to any relevant formula or structural depiction herein, some non-limiting examples of $R^{40}$ may include $R^A$, F, Cl, CN, $OR^A$, $CF_3$, $NO_2$, $NR^AR^B$, $COR^A$, $NR^ACOR^B$, $CONR^AR^B$, etc. In some embodiments, $R^{40}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{40}$ may be H.

With respect to any relevant formula or structural depiction herein, some non-limiting examples of $R^{41}$ may include $R^A$, F, Cl, CN, $OR^A$, $CF_3$, $NO_2$, $NR^AR^B$, $COR^A$, $CO_2R^A$, $NR^ACOR^B$, $CONR^AR^B$, etc. In some embodiments, $R^{41}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{41}$ may be H.

With respect to any relevant formula or structural depiction herein, some non-limiting examples of $R^{42}$ may include $R^A$, F, Cl, CN, $OR^A$, $CF_3$, $NO_2$, $NR^AR^B$, $COR^A$, $CO_2R^A$, $NR^ACOR^B$, $CONR^AR^B$, etc. In some embodiments, $R^{42}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{42}$ may be H.

With respect to any relevant formula or structural depiction herein, some non-limiting examples of $R^{43}$ may include $R^A$, F, Cl, CN, $OR^A$, $CF_3$, $NO_2$, $NR^AR^B$, $COR^A$, $CO_2R^A$, $NR^ACOR^B$, $CONR^AR^B$, etc. In some embodiments, $R^{43}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{43}$ may be H.

With respect to any relevant formula or structural depiction herein, some non-limiting examples of $R^{44}$ may include $R^A$, F, Cl, CN, $OR^A$, $CF_3$, $NO_2$, $NR^AR^B$, $COR^A$, $CO_2R^A$, $NR^ACOR^B$, $CONR^AR^B$, etc. In some embodiments, $R^{44}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{44}$ may be H.

With respect to any relevant formula or structural depiction herein, some non-limiting examples of $R^{45}$ may include $R^A$, F, Cl, CN, $OR^A$, $CF_3$, $NO_2$, $NR^AR^B$, $COR^A$, $CO_2R^A$, $NR^ACOR^B$, $CONR^AR^B$, etc. In some embodiments, $R^{45}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{45}$ may be H.

With respect to any relevant formula or structural depiction herein, some non-limiting examples of $R^{46}$ may include $R^A$, F, Cl, CN, $OR^A$, $CF_3$, $NO_2$, $NR^AR^B$, $COR^A$, $CO_2R^A$, $NR^ACOR^B$, $CONR^AR^B$, etc. In some embodiments, $R^{46}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{46}$ may be H.

With respect to any relevant formula or structural depiction herein, some non-limiting examples of $R^{47}$ may include $R^A$, F, Cl, CN, $OR^A$, $CF_3$, $NO_2$, $NR^AR^B$, $COR^A$, $CO_2R^A$, $NR^ACOR^B$, $CONR^AR^B$, etc. In some embodiments, $R^{47}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{47}$ may be H.

With respect to any relevant formula or structural depiction herein, some non-limiting examples of $R^{48}$ may include $R^A$, F, Cl, CN, $OR^A$, $CF_3$, $NO_2$, $NR^AR^B$, $COR^A$, $CO_2R^A$, $NR^ACOR^B$, $CONR^AR^B$, etc. In some embodiments, $R^{48}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{48}$ may be H.

With respect to any relevant formula or structural depiction herein, some non-limiting examples of $R^{49}$ may include $R^A$, F, Cl, CN, $OR^A$, $CF_3$, $NO_2$, $NR^AR^B$, $COR^A$, $CO_2R^A$, $NR^ACOR^B$, $CONR^AR^B$, etc. In some embodiments, $R^{49}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{49}$ may be H.

With respect to any relevant formula or structural depiction herein, some non-limiting examples of $R^{50}$ may include $R^A$, F, Cl, CN, $OR^A$, $CF_3$, $NO_2$, $NR^AR^B$, $COR^A$, $CO_2R^A$, $NR^ACOR^B$, $CONR^AR^B$, etc. In some embodiments, $R^{50}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{50}$ may be H.

With respect to any relevant formula or structural depiction herein, some non-limiting examples of $R^{51}$ may include $R^A$, F, Cl, CN, $OR^A$, $CF_3$, $NO_2$, $NR^AR^B$, $COR^A$, $CO_2R^A$, $NR^ACOR^B$, $CONR^AR^B$, etc. In some embodiments, $R^{51}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{51}$ may be H.

With respect to any relevant formula or structural depiction herein, some non-limiting examples of $R^{52}$ may include $R^A$, F, Cl, CN, $OR^A$, $CF_3$, $NO_2$, $NR^AR^B$, $COR^A$, $CO_2R^A$, $NR^ACOR^B$, $CONR^AR^B$, etc. In some embodiments, $R^{52}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{52}$ may be H.

With respect to any relevant formula or structural depiction herein, some non-limiting examples of $R^{53}$ may include $R^A$, F, Cl, CN, $OR^A$, $CF_3$, $NO_2$, $NR^AR^B$, $COR^A$, $CO_2R^A$, $NR^ACOR^B$, $CONR^AR^B$, etc. In some embodiments, $R^{53}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{53}$ may be H.

With respect to any relevant formula or structural depiction herein, some non-limiting examples of $R^{54}$ may include $R^A$, F, Cl, CN, $OR^A$, $CF_3$, $NO_2$, $NR^AR^B$, $COR^A$, $CO_2R^A$, $NR^ACOR^B$, $CONR^AR^B$, etc. In some embodiments, $R^{54}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{54}$ may be H.

With respect to any relevant formula or structural depiction herein, some non-limiting examples of $R^{55}$ may include $R^A$, F, Cl, CN, $OR^A$, $CF_3$, $NO_2$, $NR^AR^B$, $COR^A$, $CO_2R^A$, $NR^ACOR^B$, $CONR^A R^B$, etc. In some embodiments, $R^{55}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{55}$ may be H.

With respect to any relevant formula or structural depiction herein, some non-limiting examples of $R^{56}$ may include $R^A$, F, Cl, CN, $OR^A$, $CF_3$, $NO_2$, $NR^A R^B$, $COR^A$, $CO_2 R^A$, $NR^A COR^B$, $CONR^A R^B$, etc. In some embodiments, $R^{56}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{56}$ may be H.

With respect to any relevant formula or structural depiction herein, some non-limiting examples of $R^{57}$ may include $R^A$, F, Cl, CN, $OR^A$, $CF_3$, $NO_2$, $NR^A R^B$, $COR^A$, $CO_2 R^A$, $NR^A COR^B$, $CONR^A R^B$, etc. In some embodiments, $R^{57}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{57}$ may be H.

With respect to any relevant formula or structural depiction herein, some non-limiting examples of $R^{58}$ may include $R^A$, F, Cl, CN, $OR^A$, $CF_3$, $NO_2$, $NR^A R^B$, $COR^A$, $CO_2 R^A$, $NR^A COR^B$, $CONR^A R^B$, etc. In some embodiments, $R^{58}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{58}$ may be H.

With respect to any relevant formula or structural depiction herein, some non-limiting examples of $R^{59}$ may include $R^A$, F, Cl, CN, $OR^A$, $CF_3$, $NO_2$, $NR^A R^B$, $COR^A$, $CO_2 R^A$, $NR^A COR^B$, $CONR^A R^B$, etc. In some embodiments, $R^{59}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{59}$ may be H.

With respect to any relevant formula or structural depiction herein, some non-limiting examples of $R^{60}$ may include $R^A$, F, Cl, CN, $OR^A$, $CF_3$, $NO_2$, $NR^A R^B$, $COR^A$, $CO_2 R^A$, $NR^A COR^B$, $CONR^A R^B$, etc. In some embodiments, $R^{60}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{60}$ may be H.

With respect to any relevant formula or structural depiction herein, some non-limiting examples of $R^{61}$ may include $R^A$, F, Cl, CN, $OR^A$, $CF_3$, $NO_2$, $NR^A R^B$, $COR^A$, $CO_2 R^A$, $NR^A COR^B$, $CONR^A R^B$, etc. In some embodiments, $R^{61}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{61}$ may be H.

With respect to any relevant formula or structural depiction herein, some non-limiting examples of $R^{62}$ may include $R^A$, F, Cl, CN, $OR^A$, $CF_3$, $NO_2$, $NR^A R^B$, $COR^A$, $CO_2 R^A$, $NR^A COR^B$, $CONR^A R^B$, etc. In some embodiments, $R^{62}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{62}$ may be H.

With respect to any relevant formula or structural depiction herein, some non-limiting examples of $R^{63}$ may include $R^A$, F, Cl, CN, $OR^A$, $CF_3$, $NO_2$, $NR^A R^B$, $COR^A$, $CO_2 R^A$, $NR^A COR^B$, $CONR^A R^B$, etc. In some embodiments, $R^{63}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{63}$ may be H.

With respect to any relevant formula or structural depiction herein, some non-limiting examples of $R^{64}$ may include $R^A$, F, Cl, CN, $OR^A$, $CF_3$, $NO_2$, $NR^A R^B$, $COR^A$, $CO_2 R^A$, $OCOR^A N R^A COR^B$, $CONR^A R^B$, etc. In some embodiments, $R^{64}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{64}$ may be H.

With respect to any relevant formula or structural depiction herein, some non-limiting examples of $R^{65}$ may include $R^A$, F, Cl, CN, $OR^A$, $CF_3$, $NO_2$, $NR^A R^B$, $COR^A$, $CO_2 R^A$, $OCOR^A N R^A COR^B$, $CONR^A R^B$, etc. In some embodiments, $R^{65}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{65}$ may be H.

With respect to any relevant formula or structural depiction herein, some non-limiting examples of $R^{66}$ may include $R^A$, F, Cl, CN, $OR^A$, $CF_3$, $NO_2$, $NR^A R^B$, $COR^A$, $CO_2 R^A$, $OCOR^A N R^A COR^B$, $CONR^A R^B$, etc. In some embodiments, $R^{66}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{66}$ may be H.

With respect to any relevant formula or structural depiction herein, some non-limiting examples of $R^{67}$ may include $R^A$, F, Cl, CN, $OR^A$, $CF_3$, $NO_2$, $NR^A R^B$, $COR^A$, $CO_2 R^A$, $OCOR^A N R^A COR^B$, $CONR^A R^B$, etc. In some embodiments, $R^{67}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{67}$ may be H.

With respect to any relevant formula or structural depiction herein, some non-limiting examples of $R^{68}$ may include $R^A$, F, Cl, CN, $OR^A$, $CF_3$, $NO_2$, $NR^A R^B$, $COR^A$, $CO_2 R^A$, $OCOR^A N R^A COR^B$, $CONR^A R^B$, etc. In some embodiments, $R^{68}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{68}$ may be H.

With respect to any relevant formula or structural depiction herein, some non-limiting examples of $R^{69}$ may include $R^A$, F, Cl, CN, $OR^A$, $CF_3$, $NO_2$, $NR^A R^B$, $COR^A$, $CO_2 R^A$, $OCOR^A N R^A COR^B$, $CONR^A R^B$, etc. In some embodiments, $R^{69}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{69}$ may be H.

With respect to any relevant formula or structural depiction herein, some non-limiting examples of $R^{70}$ may include $R^A$, F, Cl, CN, $OR^A$, $CF_3$, $NO_2$, $NR^A R^B$, $COR^A$, $CO_2 R^A$, $OCOR^A N R^A COR^B$, $CONR^A R^B$, etc. In some embodiments, $R^{70}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{70}$ may be H.

With respect to any relevant formula or structural depiction herein, some non-limiting examples of $R^{71}$ may include $R^A$, F, Cl, CN, $OR^A$, $CF_3$, $NO_2$, $NR^A R^B$, $COR^A$, $CO_2 R^A$, $OCOR^A N R^A COR^B$, $CONR^A R^B$, etc. In some embodiments, $R^{71}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{71}$ may be H.

With respect to any relevant formula or structural depiction herein, some non-limiting examples of $R^{72}$ may include $R^A$, F, Cl, CN, $OR^A$, $CF_3$, $NO_2$, $NR^AR^B$, $COR^A$, $CO_2R^A$, $OCOR^AN$-$R^ACOR^B$, $CONR^AR^B$, etc. In some embodiments, $R^{72}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{72}$ may be H.

With respect to any relevant formula or structural depiction herein, some non-limiting examples of $R^{73}$ may include $R^A$, F, Cl, CN, $OR^A$, $CF_3$, $NO_2$, $NR^AR^B$, $COR^A$, $CO_2R^A$, $OCOR^AN$-$R^ACOR^B$, $CONR^AR^B$, etc. In some embodiments, $R^{73}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{73}$ may be H.

With respect to any relevant formula or structural depiction herein, some non-limiting examples of $R^{100}$ may include $R^A$, F, Cl, CN, $OR^A$, $CF_3$, $NO_2$, $NR^AR^B$, $COR^A$, $CO_2R^A$, $OCOR^ANR^ACOR^B$, $CONR^AR^B$, etc. In some embodiments, $R^{100}$ may be H; $C_{1-3}$ alkyl, such as methyl, ethyl, propyl isomers, cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^{100}$ may be H. In some embodiments, $R^{100}$ is optionally substituted phenyl. In some embodiments, $R^{100}$ is phenyl that is unsubstituted, or substituted phenyl with 1 or more substituents that are independently $C_{1-3}$ alkyl or $C_{1-3}$ perfluoralkyl.

Some embodiments may include one of the compounds below:

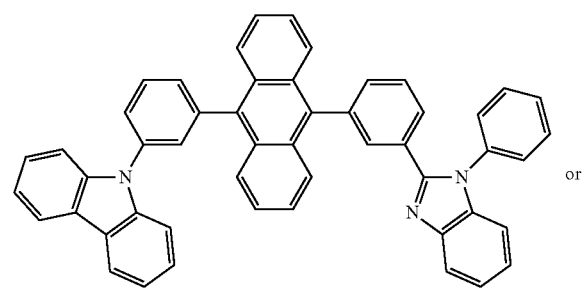

9-(3-(10-(3-(1-phenyl-1H-benzo[d]imidazol-2-yl)phenyl)anthracen-9-yl)phenyl)-9H-carbzole or

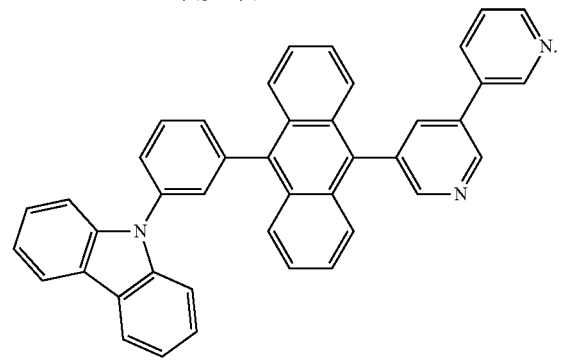

9-(3-10-[(3,3'-bipyridin]-5-yl)anthracen-9-yl)phenyl)-9H-carbazole

Some embodiments include optionally substituted Host-1 or optionally substituted Host-2.

In some embodiments, a compound described herein, such as a compound of any of Formulas 1-29, optionally substituted Host-1, or optionally substituted Host-2, may have a triplet energy of at least about 2.0 eV, at least about 2.5 eV, or about 2.5 eV to about 3.5 eV.

In some embodiments, a compound described herein, such as a compound of any of Formulas 1-29, optionally substituted Host-1, or optionally substituted Host-2, may have a phosphorescence quantum yield of at least about 10%, at least about 30%, at least about 50%, or at least about 80%, and may approach 100%.

In some embodiments, a compound described herein, such as a compound of any of Formulas 1-29, optionally substituted Host-1, or optionally substituted Host-2, may have a lowest unoccupied molecular orbital (LUMO) energy of about −2 eV to about 3 eV, about −2.2 eV to about −2.8 eV, about −2.5 eV to about −2.7 eV, about −2.56 eV, or about −2.6 eV.

In some embodiments, a compound described herein, such as a compound of any of Formulas 1-29, optionally substituted Host-1, or optionally substituted Host-2, may have a highest occupied molecular orbital (HOMO) energy of about −5 eV to about 6 eV, about −5.3 eV to about −5.8 eV, about −5.5 eV to about −5.8 eV, about −5.6 eV to about −5.7 eV, about −5.66 eV, or about −5.68 eV.

In some embodiments, a compound described herein, such as a compound of any of Formulas 1-29, optionally substituted Host-1, or optionally substituted Host-2, may have an optical band gap energy of about 2.0 eV to about 3.5 eV, about 2.5 eV to about 3.5 eV, about 2.8 eV to about 3.2 eV, about 2.8 eV to about 3.3 eV, about 2.8 eV to about 3.4 eV, about 2.9 eV to about 3.1 eV, about 3.0 eV, 3.04 eV, or 2.99 eV.

The compounds and compositions described herein can be incorporated into light-emitting devices in various ways. For example, an embodiment provides an organic component disposed between an anode and a cathode. In some embodiments, the device may be configured so that holes can be transferred from the anode to the organic component. In some embodiments, the device may be configured so that electrons can be transferred from the cathode to the organic component. The organic component may comprise the compounds and/or compositions described herein.

The anode may be a layer comprising a conventional material such as a metal, mixed metal, alloy, metal oxide or mixed-metal oxide, conductive polymer, and/or an inorganic material such as carbon nanotube (CNT). Examples of suitable metals include the Group 1 metals, the metals in Groups 4, 5, 6, and the Group 8-10 transition metals. If the anode layer is to be light-transmitting, metals in Group 10 and 11, such as Au, Pt, and Ag, or alloys thereof; or mixed-metal oxides of Group 12, 13, and 14 metals, such as indium-tin-oxide (ITO), indium-zinc-oxide (IZO), and the like, may be used. In some embodiments, the anode layer may be an organic material such as polyaniline. The use of polyaniline is described in, e.g., "Flexible light-emitting diodes made from soluble conducting polymer," *Nature*, vol. 357, pp. 477-479 (11 Jun. 1992), which is incorporated by reference herein for its relevant teachings. Examples of suitable high work function metals and metal oxides include but are not limited to Au, Pt, or alloys thereof; ITO; IZO; and the like. In some embodiments, the anode layer can have a thickness in the range of about 1 nm to about 1000 nm.

A cathode may be a layer including a material having a lower work function than the anode layer. Examples of suitable materials for the cathode layer include those selected from alkali metals of Group 1, Group 2 metals, Group 12 metals including rare earth elements, lanthanides and actinides, materials such as aluminum, indium, calcium, barium, samarium and magnesium, and combinations thereof. Li-containing organometallic compounds, LiF, and Li₂O may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, the cathode layer can have a thickness in the range of about 1 nm to about 1000 nm.

In some embodiments, the organic component may comprise at least one light-emitting layer comprising a light-emitting component, and optionally, a host. A host may comprise a compound described herein, a hole-transport material, an electron-transport material, and/or an ambipolar material. In some embodiments, the device may be configured so that holes can be transferred from the anode to the light-emitting layer. In some embodiments, the device may be configured so that electrons can be transferred from the cathode to the light-emitting layer. If present, the amount of the host in a light-emitting layer can vary. In one embodiment, the amount of a host in a light-emitting layer may be in the range of from about 1% to about 99.9% by weight of the light-emitting layer. In another embodiment, the amount of a host in a light-emitting layer may be in the range of from about 90% to about 99% by weight of the light-emitting layer. In another embodiment, the amount of a host in a light-emitting layer may be about 97% by weight of the light-emitting layer.

In some embodiments, the mass of the light-emitting component may be about 0.1% to about 10%, about 1% to about 5%, or about 3% of the mass of the light-emitting layer. In some embodiments, the light-emitting layer may be a neat light-emitting layer, meaning that the light-emitting component is about 100% by weight of the light-emitting layer, or alternatively, the light-emitting layer consists essentially of light-emitting component. The light-emitting component may be a fluorescent and/or a phosphorescent compound. In some embodiments, the light-emitting component comprises a phosphorescent material.

The light-emitting component or compound may be chosen to vary the color of the light emitted by the light-emitting device. For example, a blue light-emitting component may emit a combination of visible photons so that the light appears to have a blue quality to an observer. In some embodiments, a blue light-emitting component may emit visible photons having an average wavelength in the range of about 440 nm or about 460 nm to about 490 nm or about 500 nm. The "average wavelength" of visible photons may include, when referring to the visible emission spectrum of a compound, the wavelength wherein the area under the curve for the part of the visible spectrum having a lower wavelength than the average wavelength is about equal to the area under the curve for the part of the visible spectrum having a higher wavelength than the average wavelength. Some non-limiting examples of compounds which may form part or all of a blue light-emitting component include iridium coordination compounds such as: bis-{2-[3,5-bis(trifluoromethyl)phenyl]pyridinato-N,C2'}iridium(III)-picolinate, bis(2-[4,6-difluorophenyl]pyridinato-N,C2')iridium (III) picolinate, bis(2-[4,6-difluorophenyl]pyridinato-N,C2')iridium(acetylacetonate), Iridium (III) bis(4,6-difluorophenylpyridinato)-3-(trifluoromethyl)-5-(pyridine-2-yl)-1,2,4-triazolate, Iridium (III) bis (4,6-difluorophenylpyridinato)-5-(pyridine-2-yl)-1H-tetrazolate, bis[2-(4,6-difluorophenyl)pyridinato-N,C²']iridium (III)tetra(1-pyrazolyl)borate, etc. The structures corresponding to these compounds are as follows:

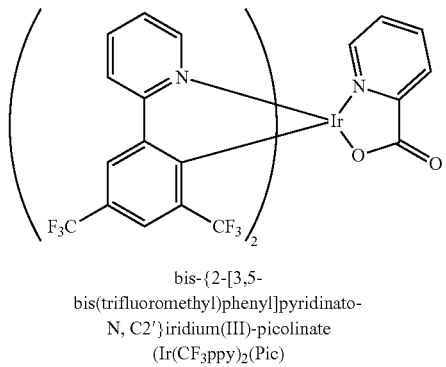

bis-{2-[3,5-bis(trifluoromethyl)phenyl]pyridinato-N, C2'}iridium(III)-picolinate (Ir(CF₃ppy)₂(Pic))

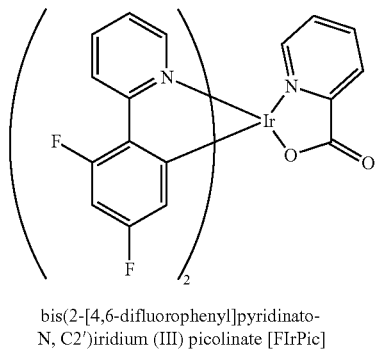

bis(2-[4,6-difluorophenyl]pyridinato-N, C2')iridium (III) picolinate [FIrPic]

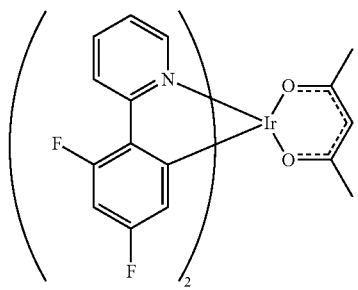

bis(2-[4,6-difluorophenyl]pyridinato-N, C2')iridium(acetylacetonate) [FIr(acac)]

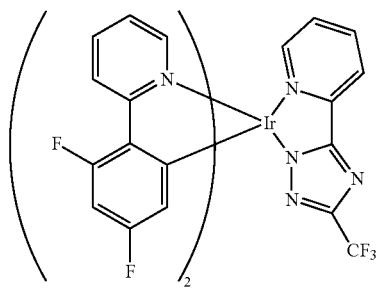

Iridium (III) bis(4,6-difluorophenylpyridinato)-3-(trifluoromethyl)-5-(pyridine-2-yl)-1,2,4-triazolate (FIrtaz)

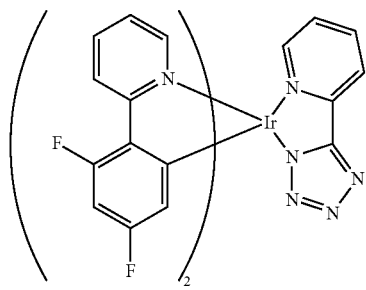

Iridium (III) bis(4,6-difluorophenylpyridinato)-5-(pyridine-2-yl)-1H-tetrazolate (FIrN4)

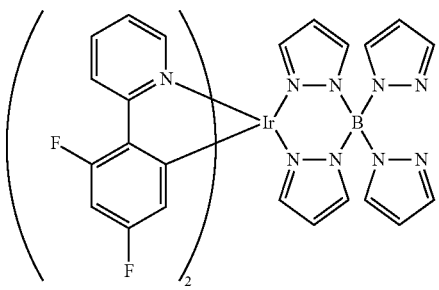

bis[2-(4,6-difluorophenyl)pyridinato-N, C²]iridium(III)tetra(1-pyrazolyl)borate (Fir6)

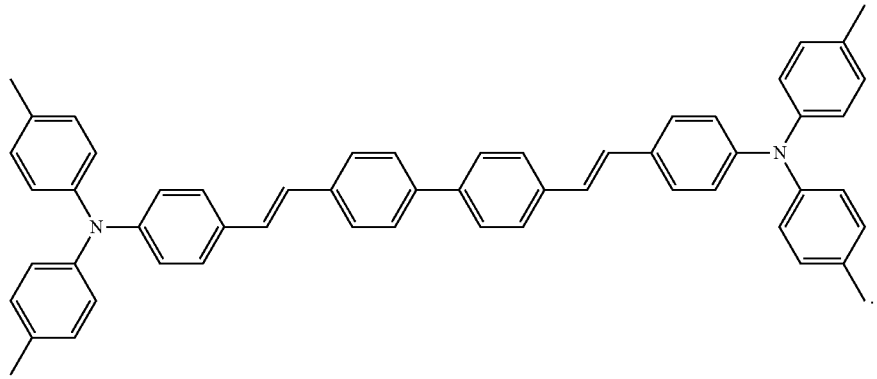

4,4'-(1E, 1'E)-[1,1'-biphenyl]-4,4'-diylbis(ethene-2,1-diyl))bis(N,N-di-p-tolylaniline) (DPAVBi)

The thickness of a light-emitting layer may vary. In one embodiment, a light-emitting layer may have a thickness in the range of from about 1 nm to about 150 nm or about 200 nm.

In some embodiments, the light-emitting device may emit white light. A light-emitting layer may be configured to emit white light by including a white light emitter, or a combination of colored emitters which have a combined emission that appears white. Alternatively, a combination of different colored light-emitting layers may be configured to emit white light.

In some embodiments, the organic component may further comprise a hole-transport layer disposed between the anode and the light-emitting layer. The hole-transport layer may comprise at least one hole-transport material. In some embodiments, the hole-transport material comprises at least one of an aromatic-substituted amine, a carbazole, a polyvinylcarbazole (PVK), e.g. poly(9-vinylcarbazole); polyfluorene; a polyfluorene copolymer; poly(9,9-di-n-octylfluorene-alt-benzothiadiazole); poly(paraphenylene); poly[2-(5-cyano-5-methylhexyloxy)-1,4-phenylene]; a benzidine; a phenylenediamine; a phthalocyanine metal complex; a polyacetylene; a polythiophene; a triphenylamine; copper phthalocyanine; 1,1-Bis(4-bis(4-methylphenyl)aminophenyl)cyclohexane; 2,9-Dimethyl-4,7-diphenyl-1,10-phenanthroline; 3,5-Bis(4-tert-butyl-phenyl)-4-phenyl[1,2,4]triazole; 3,4,5-Triphenyl-1,2,3-triazole; 4,4',4'-tris(3-methylphenylphenylamino)triphenylamine (MTDATA); N,N'-bis(3-methylphenyl)N,N'-diphenyl-[1,1'-biphenyl]-4,4'-diamine (TPD); 4,4'-bis[N-(naphthyl)-N-phenyl-amino]biphenyl (α-NPD); 4,4',4"-tris(carbazol-9-yl)-triphenylamine (TCTA); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); Bis[4-(p,p'-ditolyl-amino)phenyl]diphenylsilane (DTASi); 2,2'-bis(4-carbazolylphenyl)-1,1'-biphenyl (4CzPBP); N,N'N"-1,3,5-tricarbazoloylbenzene (tCP); N,N'-bis(4-butylphenyl)-N,N'-bis(phenyl)benzidine; or the like.

In some embodiments, the organic component may further comprise an electron-transport layer disposed between the cathode and the light-emitting layer. In some embodiments, the electron-transport layer may comprise a compound described herein. Other electron-transport materials may be included, such as 2-(4-biphenylyl)-5-(4-tert-butylphenyl)-1,3,4-oxadiazole (PBD); 1,3-bis(N,N-t-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq$_3$); and 1,3,5-tris(2-N-phenylbenzimidazolyl)benzene; 1,3-bis[2-(2,2'-bipyridine-6-yl)-1,3,4-oxadiazo-5-yl]benzene (BPY-OXD); 3-phenyl-4-(1'-naphthyl)-5-phenyl-1,2,4-triazole (TAZ), 2,9-dimethyl-4,7-diphenyl-phenanthroline (bathocuproine or BCP); and 1,3,5-tris[2-N-phenylbenzimidazol-z-yl]benzene (TPBI). In some embodiments, the electron transport layer may be aluminum quinolate (Alq$_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI or TPBi), or a derivative or a combination thereof.

If desired, additional layers may be included in the light-emitting device. These additional layers may include an electron injection layer (EIL), a hole-blocking layer (HBL), an exciton-blocking layer (EBL), and/or a hole-injection layer (HIL). In addition to separate layers, some of these materials may be combined into a single layer.

In some embodiments, the light-emitting device can include an electron injection layer between the cathode layer and the light emitting layer. In some embodiments, the lowest unoccupied molecular orbital (LUMO) energy level of the electron injection material(s) is high enough to prevent it from receiving an electron from the light emitting layer. In other embodiments, the energy difference between the LUMO of the electron injection material(s) and the work function of the cathode layer is small enough to allow the electron injection layer to efficiently inject electrons into the light-emitting layer from the cathode. A number of suitable electron injection materials are known to those skilled in the art. Examples of suitable electron injection material(s) include but are not limited to, an optionally substituted compound selected from the following: LiF, CsF, Cs doped into electron transport material as described above or a derivative or a combination thereof.

In some embodiments, the device can include a hole-blocking layer, e.g., between the cathode and the light-emitting layer. Various suitable hole-blocking materials that can be included in the hole-blocking layer are known to those skilled in the art. Suitable hole-blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4] triazole, 2,9-dimethyl-4,7-diphenyl-1,10-phenanthroline, and 1,1-bis(4-bis(4-methylphenyl)aminophenyl)-cyclohexane.

In some embodiments, the light-emitting device can include an exciton-blocking layer; e.g., between the light-emitting layer and the anode. In an embodiment, the band gap energy of the material(s) that comprise exciton-blocking layer may be large enough to substantially prevent the diffusion of excitons. A number of suitable exciton-blocking materials that can be included in the exciton-blocking layer are known to those skilled in the art. Examples of material(s) that can compose an exciton-blocking layer include an optionally substituted compound selected from the following: aluminum quinolate ($Alq_3$), 4,4'-bis[N-(naphthyl)-N-phenyl-amino]biphenyl ($\alpha$-NPD), 4,4'-N,N'-dicarbazole-biphenyl (CBP), and bathocuproine (BCP), and any other material(s) that have a large enough band gap to substantially prevent the diffusion of excitons.

In some embodiments, the light-emitting device can include a hole-injection layer between the light-emitting layer and the anode. Various suitable hole-injection materials that can be included in the hole-injection layer are known to those skilled in the art. Exemplary hole-injection material(s) include an optionally substituted compound selected from the following: a polythiophene derivative such as poly(3,4-ethylenedioxythiophene (PEDOT)/polystyrene sulphonic acid (PSS), a benzidine derivative such as N,N,N',N'-tetraphenyl-benzidine, poly(N,N'-bis(4-butylphenyl)-N,N'-bis(phenyl) benzidine), a triphenylamine or phenylenediamine derivative such as N,N'-bis(4-methylphenyl)-N,N'-bis(phenyl)-1,4-phenylenediamine, 4,4',4"-tris(N-(naphthylen-2-yl)-N-phenylamino)triphenylamine, an oxadiazole derivative such as 1,3-bis(5-(4-diphenylamino)phenyl-1,3,4-oxadiazol-2-yl) benzene, a polyacetylene derivative such as poly(1,2-bis-benzylthio-acetylene), and a phthalocyanine metal complex derivative such as phthalocyanine copper (CuPc). In some embodiments, hole-injection materials, while still being able to transport holes, may have a hole mobility substantially less than the hole mobility of conventional hole transport materials.

Light-emitting devices comprising the compounds described herein can be fabricated using techniques known in the art, as informed by the guidance provided herein. For example, a glass substrate can be coated with a high work functioning metal such as ITO which can act as an anode. After patterning the anode layer, a hole-injection and/or hole-transport layer may be deposited on the anode in that order. A light-emitting layer that includes a light-emitting component can be deposited on the anode, the hole-transport layer, or the hole-injection layer. The light-emitting layer may contain a compound described herein, and/or a compound described herein may be part of an electron-transport layer and/or an electron-injecting layer, deposited in that order, or may be part of an electron-injecting and electron-transport layer. The cathode layer, comprising a low work functioning metal (e.g., Mg:Ag), can then be deposited, e.g., by vapor deposition or sputtering. The device may also contain an exciton-blocking layer, an electron blocking layer, a hole blocking layer, a second light-emitting layer, or other layers that can be added to the device using suitable techniques.

An example of a configuration of a device comprising a compound as described herein is shown in FIG. 1. The device comprises the following layers in the order given: an ITO/Glass anode 5, a PEDOT/PSS hole-injection layer 10, a hole-transport layer (TCTA) 15, a light-emitting layer 20, an electron-transport layer (TPBI) 30, and a LiF/Al cathode 35.

In some embodiments, the OLED may be made by a wet process such as a process that comprises at least one of spraying, spin coating, drop casting, inkjet printing, screen printing, etc. Some embodiments provide a composition which may be a liquid suitable for deposition onto a substrate. The liquid may be a single phase, or may comprise one or more additional solid or liquid phases dispersed in it. The liquid typically comprises a light-emitting compound, a host material described herein and a solvent.

EXAMPLES

The following are examples of some methods that may be used to prepare and use the compounds described herein.

Example 1

Synthesizing Host Materials

Example 1.1.1

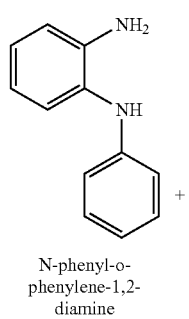

N-phenyl-o-phenylene-1,2-diamine

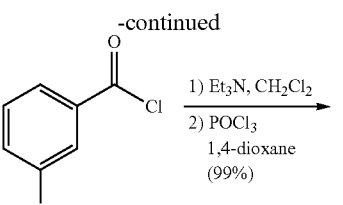

3-bromobenzoyl chloride

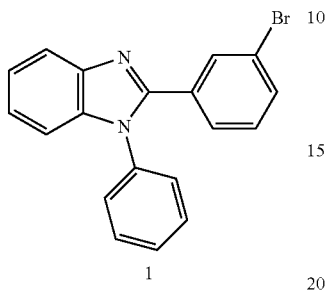

1

2-(3-bromophenyl)-1-phenyl-1H-benzo[d]imidazole (1)

Compound 1 was prepared as follows: to a stirring solution of N-phenyl-o-phenylene-1,2-diamine (4.470 g, 24.26 mmol) in anhydrous $CH_2Cl_2$ (116 mL) was added 3-bromobenzoyl chloride (3.14 mL, 23.8 mmol) dropwise via syringe, followed by dropwise addition of triethylamine ($Et_3N$) (6.78 mL). Stirring was continued at room temperature (RT) until thin layer chromatography (TLC) ($SiO_2$, 4:1 hexanes-ethyl acetate) indicated consumption of the starting material (23 h.). The reaction was then washed with saturated $NaHCO_3$, water and brine, dried over $MgSO_4$, filtered and concentrated in vacuo. The crude intermediate was then dissolved in anhydrous 1,4-dioxane (105 mL) and heated to 75° C. Upon completely dissolving, phosphorus oxychloride (6.70 mL, 69.9 mmol) was added to the solution slowly via syringe and the reaction then maintained at 115° C. Upon completion (2 h.), the solution was cooled to RT and poured over a mixture of ethyl acetate (about 500 mL) and water (about 400 mL). The organics were then washed with saturated $NaHCO_3$, $H_2O$ and brine, dried over $MgSO_4$, filtered and concentrated in vacuo. Purification of the crude product by flash chromatography ($SiO_2$, 9:1 hexanes-acetone) provided compound 1 (8.30 g, 99%) as an off-white solid.

Example 1.1.2

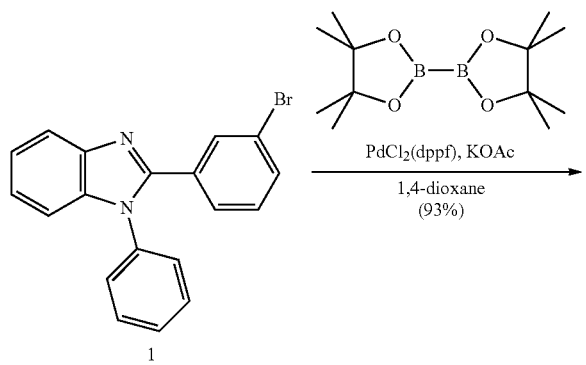

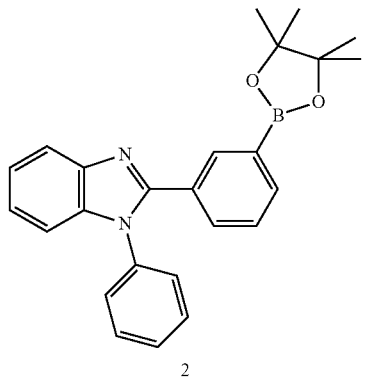

1-phenyl-2-(3-(4,4,5,5-tetramethyl-1,3,2-dioxaborolan-2-yl)phenyl)-1H-benzo[d]imidazole (2)

A procedure from the literature (Ge, Z.; Hayakawa, T.; Ando, S.; Ueda, M.; Akiike, T.; Miyamoto, H.; Kajita, T.; Kakimoto, M.; *Chem. Mater.* 2008, 20(7), 2532-2537; which is incorporated by reference herein for its relevant teachings) was modified as follows: a mixture of Compound 1 (5.000 g, 14.32 mmol), bis(pinacolato)diboron (7.635 g, 30.07 mmol), [1,1'-bis(diphenylphosphino)-ferrocene]dichloropalladium (II) (0.629 g, 0.859 mmol), potassium acetate (4.215 g, 42.95 mmol) and 1,4-dioxane (100 mL) was degassed with argon for 50 min. while stirring. The reaction mixture was then maintained under argon at 80° C. while stirring for 17 h. Upon confirming completion via TLC ($SiO_2$, 4:1 hexanes-ethyl acetate), the reaction was cooled to RT and about 120 mL EtOAc added. The mixture was then filtered through a short silica gel plug (about ½ in.) and the filtrate washed copiously with EtOAc (about 200 mL). The organics were then washed with saturated $NaHCO_3$, water and brine, dried over $MgSO_4$, filtered and concentrated in vacuo. Purification of the crude product via flash chromatography ($SiO_2$, 4:1 to 7:3 hexanes:ethyl acetate) afforded compound 2 (5.28 g, 93%) as an off-white, powdery solid.

Example 1.1.3

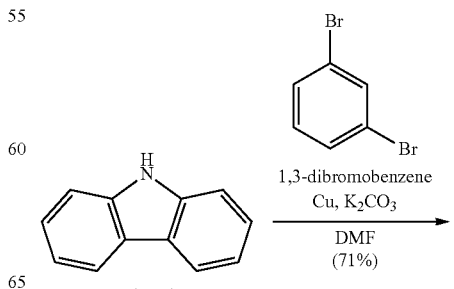

carbazole

9-(3-(4,4,5,5-tetramethyl-1,3,2-dioxaborolan-2-yl) phenyl)-9H-carbazole (Compound 4)

Compound 4 was prepared as follows: a mixture of compound 3 (see Kido, J.; Su, S. -J.; Sasabe, H.; and, Takeda, T., Chem. Mater. 2008, 20(5), 1691-1693, which is incorporated by reference herein for its relevant teachings) (5.45 g, 16.9 mmol), bis(pinacolato)diboron (9.020 g, 35.52 mmol), [1,1'-bis(diphenylphosphino)-ferrocene]dichloropalladium(II) (0.743 g, 1.02 mmol), potassium acetate (4.980, 50.75 mmol) and anhydrous toluene (110 mL) was degassed with argon for 1 h. while stirring. The reaction mixture was then maintained under argon at 100° C. while stirring for 25 h. until TLC (SiO$_2$, 4:1 hexanes-dichloromethane) confirmed consumption of the starting material. Upon completion, the reaction was cooled to RT and about 500 mL ethyl acetate added. The organics were then washed with saturated NaHCO$_3$, H$_2$O and brine, dried over MgSO$_4$, filtered and concentrated in vacuo. The crude product was purified via flash chromatography (SiO$_2$, 4:1 hexanes-dichloromethane to 100% dichloromethane) to afford Compound 4 (4.26 g, 68%) as a white solid.

Example 1.1.5

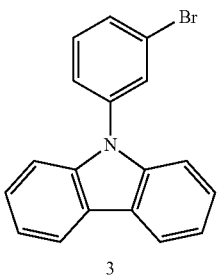

9-(3-bromophenyl)-9H-carbazole (Compound 3).
Compound 3

(see Kido, J.; Su, S. -J.; Sasabe, H.; Takeda, T.; Chem. Mater. 2008, 20(5), 1691-1693, which is incorporated by reference herein for its relevant teachings) was prepared as follows: a mixture of carbazole (4.000 g, 23.92 mmol), 1,3-dibromobenzene (14.11 g, 59.81 mmol), K$_2$CO$_3$ (9.919 g, 71.77 mmol), copper powder (4.561 g, 71.77 mmol) and anhydrous N,N-dimethylformamide (DMF) (120 mL) was degassed with argon for 1 h. while stirring. The reaction mixture was then maintained under argon at 130° C. while stirring for 4 days until TLC (SiO$_2$, 4:1 hexanes-dichloromethane) indicated consumption of the starting material. Upon cooling to RT, about 300 mL dichloromethane was added, the crude mixture filtered, the filtrant wash with an additional 200 mL dichloromethane, and the filtrate concentrated in vacuo. The resulting residue was then purified by flash chromatography (SiO$_2$, hexanes) to yield Compound 3 (5.47 g, 71%) as a colorless oil.

Example 1.1.4

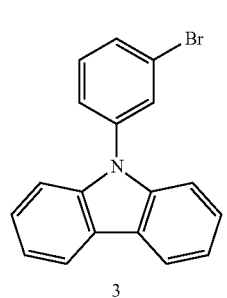
3

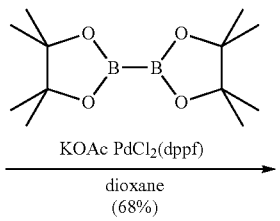
KOAc PdCl$_2$(dppf)
dioxane
(68%)

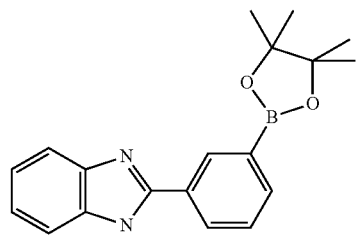
2

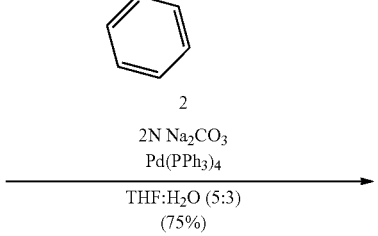
9,10-dibromoanthracene

2N Na$_2$CO$_3$
Pd(PPh$_3$)$_4$
THF:H$_2$O (5:3)
(75%)

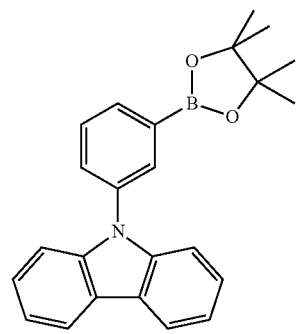
4

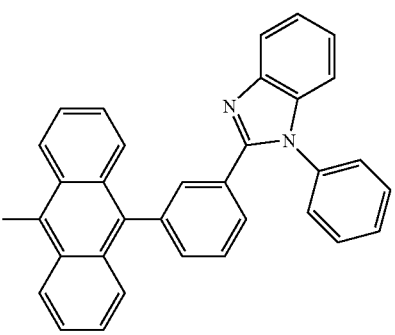
5

2-(3-(10-bromoanthracen-9-yl)phenyl)-1-phenyl-1H-benzo[d]imidazole (Compound 5)

Compound 5 (see WO 2007046658 A1, US 20070205412 A1 and WO 2007086695 A1, which are incorporated by reference herein for their relevant teachings) was prepared as follows: a mixture of Compound 2 (5.270 g, 13.30 mmol), 9,10-dibromoanthracene (13.41 g, 39.90 mmol), tetrakis(triphenylphosphine)palladium(0) (0.922 g, 0.798 mmol), $Na_2CO_3$ (9.539 g, 90.00 mmol), $H_2O$ (90 mL) and tetrahydrofuran (THF) (150 mL) was degassed with argon for 1.5 h. while stirring. The reaction mixture was then maintained under argon at 85° C. while stirring for 46 h. Upon completion, the reaction was cooled to RT and poured over dichloromethane (about 500 mL). The soluble organics were then washed with $H_2O$ and brine, dried over $MgSO_4$, filter and concentrated in vacuo. The crude product was purified via flash chromatography ($SiO_2$, 100% dichloromethane) to provide Compound 5 (5.25 g, 75%) as a light yellow solid.

Example 1.1.6

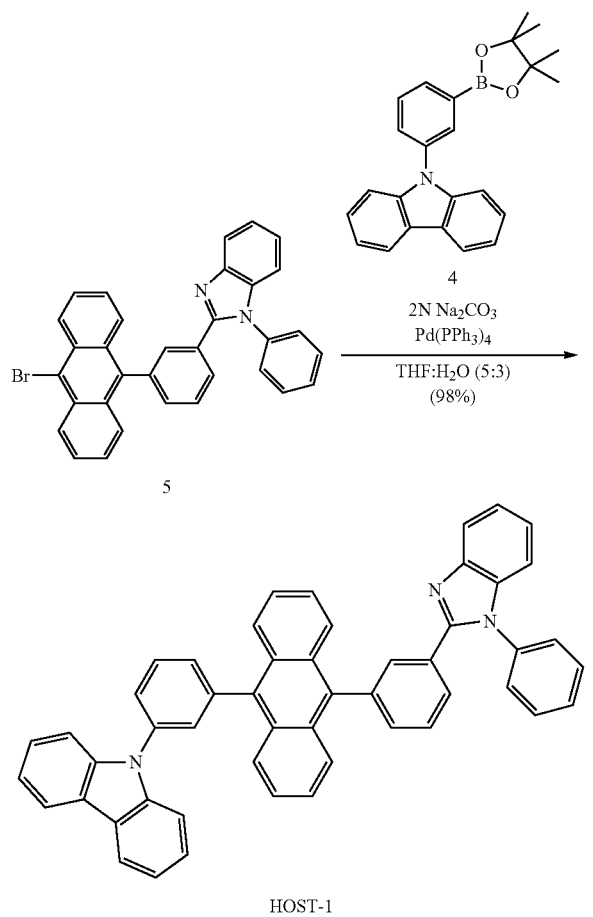

9-(3-(10-(3-(1-phenyl-1H-benzo[d]imidazol-2-yl)phenyl)anthracen-9-yl)phenyl)-9H-carbazole (Host-1)

Following the procedure for Compound 5, compound 4 (3.617 g, 9.795 mmol), Compound 5 (5.147 g, 9.795 mmol), tetrakis(triphenylphosphine)palladium(0) (0.566 g, 0.490 mmol), $Na_2CO_3$ (6.359 g, 60.00 mmol), $H_2O$ (60 mL) and THF (100 mL) yielded Host-1 (6.61 g, 98%) as an off-white solid.

Example 1.2.1

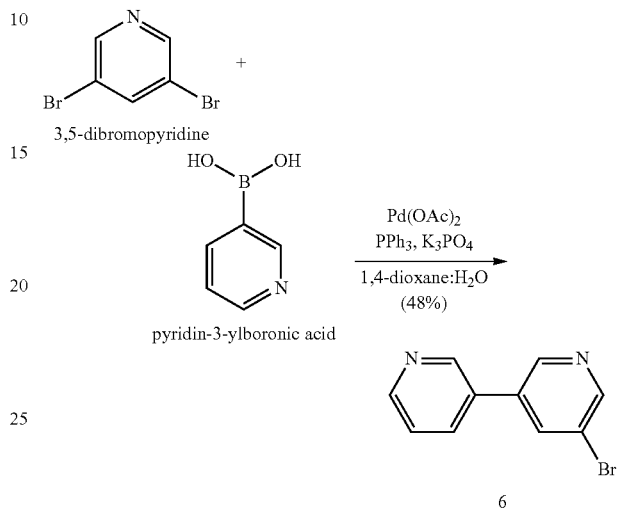

5-bromo-3,3'-bipyridine (Compound 6)

Compound 6 (see WO2009/009756) was prepared as follows: a mixture of 3,5-dibromopyridine (10.6 g, 44.7 mmol), pyridin-3-ylboronic acid (5.50 g, 44.7 mmol), palladium(II) acetate (0.550 g, 2.45 mmol), triphenylphosphine (2.50 g, 9.53 mmol), potassium phosphate tribasic (19.0 g, 89.5 mmol), $H_2O$ (45 mL) and 1,4-dioxane (200 mL) was degassed with argon for 2 h. while stirring. The reaction mixture was then maintained under argon at reflux (120° C.) while stirring for 1.5 h. Upon confirming consumption of the starting material by TLC ($SiO_2$, 7:3 dichloromethane-acetone), the reaction was cooled to RT and poured over ethyl acetate (about 400 mL). The organic phase was then washed with saturated $NaHCO_3$, $H_2O$ and brine, dried over $MgSO_4$, filter and concentrated in vacuo. The crude product was purified via flash chromatography ($SiO_2$, 4:1 dichloromethane-acetone) to provide Compound 6 (5.03 g, 48%) as a white solid.

Example 1.2.2

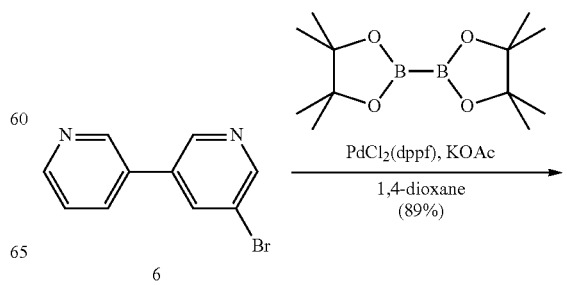

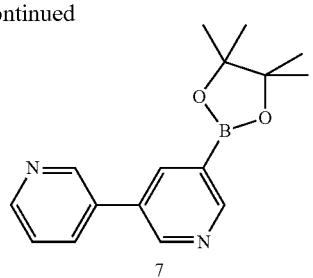

5-(4,4,5,5-tetramethyl-1,3,2-dioxaborolan-2-yl)-3,3'-bipyridine (Compound 7)

A mixture of Compound 6 (3.604 g, 15.33 mmol), bis(pinacolato)diboron (4.282 g, 16.86 mmol), [1,1'-bis(diphenylphosphino)-ferrocene]dichloropalladium(II) (0.673 g, 0.920 mmol), potassium acetate (4.514 g, 45.99 mmol) and 1,4-dioxane (100 mL) was degassed with argon at 30° C. for 90 min. while stirring. The reaction mixture was then maintained under argon at 115° C. while stirring for 3 h. Upon confirming consumption of the starting material by TLC ($SiO_2$, 7:3 dichloromethane-acetone), the reaction was cooled to RT and about 150 mL dichloromethane was added. The mixture was then filtered, the filtrant washed copiously with dichloromethane (about 200 mL) and the filtrate concentrated in vacuo. The crude product was then taken up in hot hexanes, filtered, the filtrate saved and this process repeated on the filtrant (2×). The combined filtrates were then concentrated and recrystallization from hexanes afforded Compound 7 (3.84 g, 89%) as an off-white solid.

Example 1.2.3

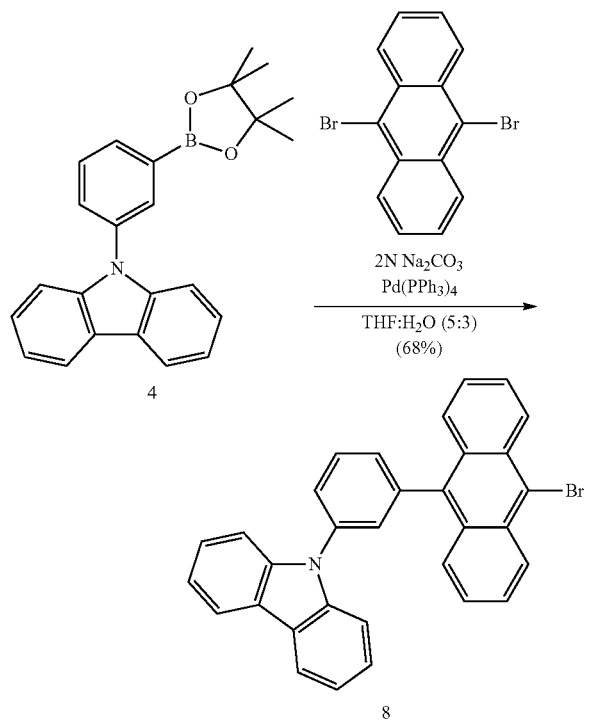

9-(3-(10-bromoanthracen-9-yl)phenyl)-9H-carbazole (Compound 8)

Following the procedure as outlined above for synthesizing Compound 5, Compound (2.686 g, 7.274 mmol), 9,10-dibromoanthracene (7.333 g, 21.82 mmol), tetrakis(triphenylphosphine)palladium(0) (0.420 g, 0.364 mmol), $Na_2CO_3$ (9.539 g, 90.00 mmol), $H_2O$ (90 mL) and THF (150 mL) yielded Compound 8 (2.45 g, 68%) as a light yellow solid after flash chromatography ($SiO_2$, 19:1 to 9:1 hexanes-dichloromethane).

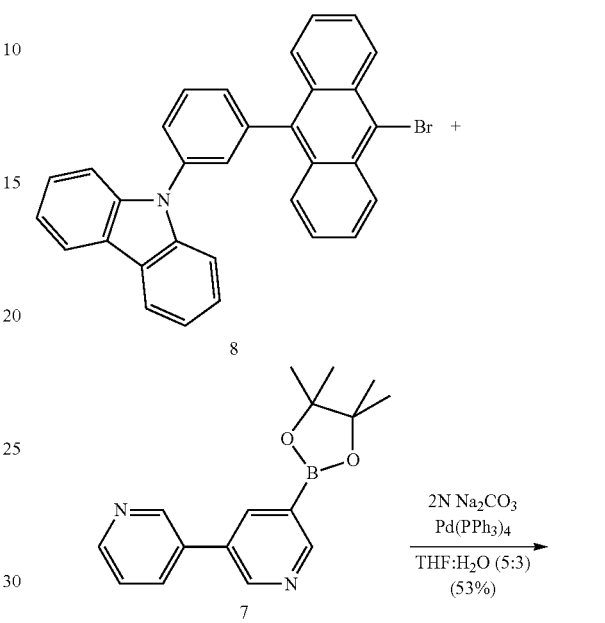

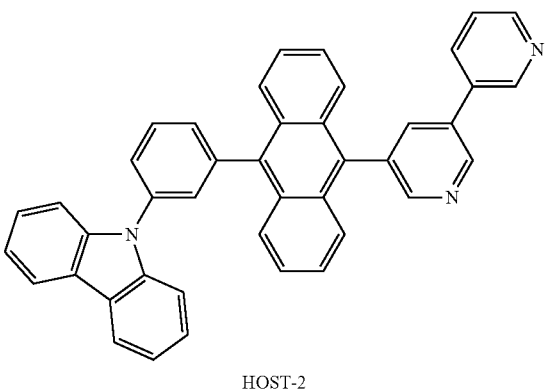

9-(3-(10-([3,3'-bipyridin]-5-yl)anthracen-9-yl)phenyl)-9H-carbazole (Host-2)

Following the procedure outlined above for synthesis of Compound 5, Compound 7 (1.140 g, 4.040 mmol), Compound 5 (1.836 g, 3.684 mmol), tetrakis(triphenylphosphine)palladium(0) (0.233 g, 0.202 mmol), $Na_2CO_3$ (2.014 g, 19.00 mmol), $H_2O$ (19 mL) and THF (31 mL) yielded Host-2 (1.23 g, 53%) as a yellow solid after flash chromatography ($SiO_2$, 100% ethyl acetate).

Example 2

Physical Properties of the Described Materials

Example 2.1.1

Photoluminescence (PL) spectra were recorded on a FluoroMax-3 fluorescence spectrophotometer (Horiba Jobin Yvon, Edison, N.J., USA). 2-ethyltetrahydrofuran (2-eTHF) (Aldrich, spectroscopic grade) was used as received from the manufacturer. 2 M (2 mg of sample/1 mL of 2-eTHF) was prepared and then transferred to quartz tube prior to measurement. Then, the sample was frozen by liquid nitrogen at 77K. Phosphorescent emission spectrum was recorded and the highest-energy vibronic band was determined to calculate triplet (T1) energy level. [What were the values of T1 energy?] [Can you estimate the phosphorescence quantum yield?]

Example 2.1.2

Cyclic voltammetry (CV) was carried out in nitrogen-purged anhydrous N,N-dimethylformamide (DMF) (Aldrich) at room temperature with Echo-Chemie potentiostat/galvanostat (Echo Chemie/Metrohm Autolabe B.V., Utrecht, the Netherlands). Tetra-n-butylammonium hexafluorophosphate (TBAPF6) and DMF were purchased from Aldrich and used as received from the manufacturer. Supporting electrolyte solution (0.1 M) with TBAPF6 and analyte, e.g., Host-1 (0.1 mM) in DMF, was used for the CV study. Formal potentials were calculated as the average of cyclic voltammetric anodic and cathodic peaks and ferrocenium-ferrocene (Fc+/Fc) as the internal standard was introduced to calibrate HOMO (highest occupied molecular orbital) and LUMO (lowest unoccupied molecular orbital) energy at each experiment. A scan rate of 100 mV/s was used unless otherwise indicated.

Example 2.1.3

Triplet ($T_1$) Energy Calculation

Triplet energy was recorded on a FloroMax-3 spectrometer (Jobin Yvon Horiba, Edison, N.J.) with phosphorescence spectra at 77K. It was determined by the highest-energy vibronic sub-band of the phosphorescence spectra of the desired compound and its wavelength was then converted to triplet energy (eV).

Example 2.1.4

HOMO/LUMO Energy Calculation

HOMO energy was directly determined by oxidation potential of respective compound with respect to redox of ferrocene/ferrocenium in anodic scan in DMF. Potential difference between the respective compound and ferrocen/ferrocenium was determined. Therefore, using vacuum level of ferrocene as the so determined difference, the HOMO of desired compound was determined. The respective LUMO energy was then determined by reduction potential of respective compound with respect to redox of ferrocene/ferrocenium in cathodic scan in DMF. Optical band gap energy of Eg (eV) was estimated by on-set value of UV-vis spectroscopy, 3.04 eV and 2.99 eV, respectively, were measured for Host-1 and Host-2 and then LUMO was calculated as set forth in Table 1.

TABLE 1

|  | HOMO | LUMO | µem | Tg |
|---|---|---|---|---|
| Host-1 | −5.66 | −2.56 | $1.60e^{-5}$ fit | 149 |
| Host-2 | −5.68 | −2.6 | $7.7e^{-5}$ fit | 132 |

Example 3

Example of OLED Device Configuration and Performance (Device A)

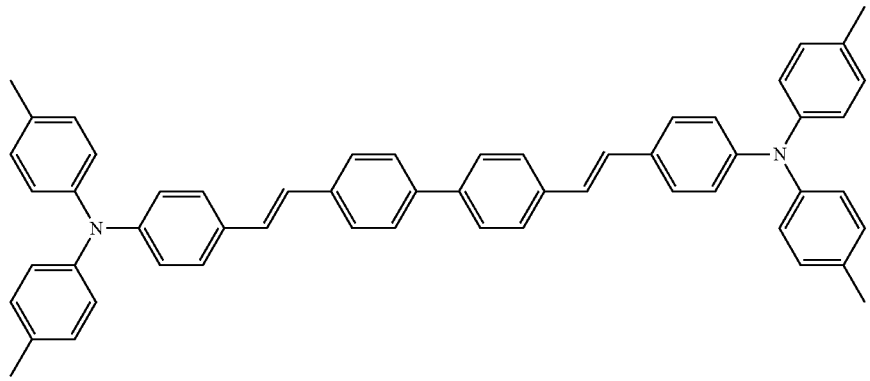

4,4'-((1E,1'E)-[1,1'-biphenyl]-4,4'-diylbis(ethene-2,1-diyl))bis(N,N-di-p-tolyaniline)
DVAVBi A light-emitting device is fabricated in the following manner. The ITO substrates having sheet resistance of about 14 ohm/sq are cleaned ultrasonically and sequentially in detergent, water, acetone and then IPA; and then dried in an oven at about 80° C. for about 30 min. under ambient environment. Substrates are baked at about 200° C. for about 1 hour in an ambient environment, then under UV-ozone treatment for about 30 minutes. PEDOT:PSS (hole-injection material) is then spin-coated on the annealed substrate at about 4000 rpm for about 30 sec. The coated layer is then baked at about 150° C. for 30 min. in an ambient environment, followed by baking at 200° C. for 30 min. inside a glove box ($N_2$ environment). The substrate is then transferred into a vacuum chamber, where 4,4',4"-tri(N-carbazolyl)triphenylamine (TCTA; i.e., the hole transporting material) is vacuum deposited at a rate of about 0.1 nm/s under a base pressure of about $2\times10^{-7}$ torr. "DVAVBi" (10 wt %) is co-deposited as an emissive layer with Host-1 host material at about 0.01 nm/s DVAVBi and about 0.10 nm/s. Host-1, to make the appropriate thickness ratio. 1,3,5-Tris(1-phenyl-1H-benzimidazol-)2-yl)benzene (TPBI) is then deposited at a rate of about 0.1 nm/s. on the emissive layer. A layer of lithium fluoride (LiF; electron injection material) is deposited at a rate of about 0.005 nm/s. followed by deposition of the cathode as Aluminium (Al) at about 0.3 nm/s. The representative device structure is: ITO (about 150 nm thick)/PEDOT:PSS (about 40 nm thick)/TCTA (about 40 nm thick)/Host-1:DPAVBi (about 30 nm thick)/TPBI (about 30 nm thick)/LiF (about 0.5 nm thick)/Al (about 100 nm thick). The device is then encapsulated with a glass cap to cover the emissive area of the OLED device in order to protect from moisture, oxidation or mechanical damage. Additional devices are prepared in the same manner, using Host-2 instead of Host-1. Each individual device has an area of about 0.14 $cm^2$. The devices made in the above described manner are tested for device efficiency. In addition, the power efficiency (lm/W) of the device is calculated, to illustrate the efficacy of the described materials as host materials.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained.

At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

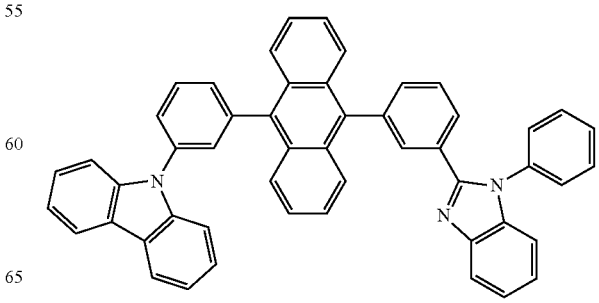

20. The device of claim 14, wherein the compound is:
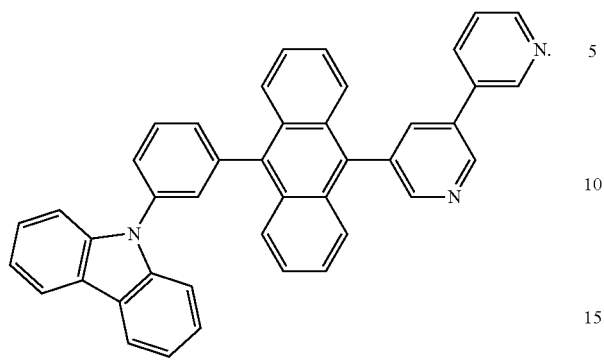

What is claimed is:

1. A compound represented by a formula:

wherein An is optionally substituted anthracenylene;
Ph$^1$ and Ph$^e$ are independently a bond or optionally substituted phenylene;
HT$^2$ is optionally substituted carbazolyl, optionally substituted phenylnaphthylamine, or optionally substituted diphenylamine; and,
ET$^2$ is an optionally substituted 3,3'-bipyridin-5-yl.

2. The compound claim 1, wherein HT$^2$ is represented by a formula:

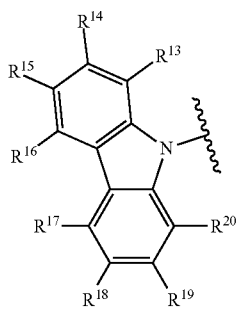

wherein R$^{13}$, R$^{14}$, R$^{15}$, R$^{16}$, R$^{17}$, R$^{18}$, R$^{19}$, and R$^{20}$ are independently H, C$_{1-3}$ alkyl, or C$_{1-3}$ perfluoroalkyl.

3. The compound of claim 1, wherein Ph$^1$ is a bond.
4. The compound of claim 1, wherein Ph$^1$ is m-phenylene.
5. The compound of claim 1, wherein Ph$^2$ is a bond.
6. The compound of claim 1, wherein Ph$^2$ is m-phenylene.
7. The compound of claim 1, wherein An is optionally substituted 9,10-anthracenylene.
8. A compound that is an optionally substituted 9-(3-(10-(3-(1-phenyl-1H-benzo[d]imidazol-2-yl)phenyl)anthracen-9-yl)phenyl)-9H-carbazole or an optionally substituted 9-(3-(10-([3,3'-bipyridin]-5-yl)anthracen-9-yl)phenyl)-9H-carbazole.
9. The compound of claim 1, wherein if any substituents are present, each substituent independently has a molecular weight of 15 g/mol to 1000 g/mol.
10. The compound of claim 8, wherein the compound is:

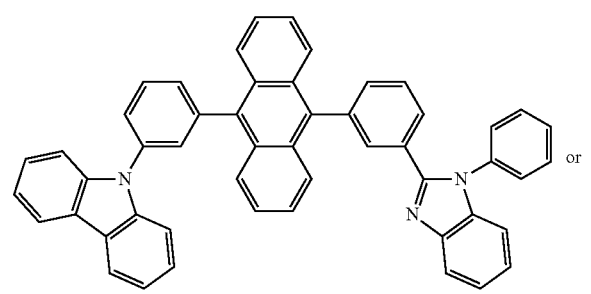 or

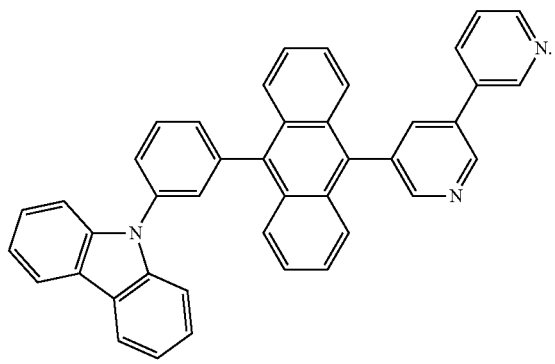

11. The compound of claim 1, having a lowest unoccupied molecular orbital (LUMO) energy of about −2.5 eV to about −2.7 eV.

12. The compound of claim 8, having a highest occupied molecular orbital (HOMO) energy about −5.5 eV to about −5.8 eV.

13. The compound of claim 9, having optical band gap energy of about 2.8 eV to about 3.4 eV.

14. An organic light-emitting diode device comprising:
a cathode;
an anode; and,
a light-emitting layer disposed between and electrically connected to the anode and the cathode, wherein the light-emitting layer comprises a compound of claim 8.

15. The device of claim 14 further comprising a hole-transport layer between the anode and the light-emitting layer and an electron-transport layer between the cathode and the light-emitting layer.

16. The compound of claim 8, wherein if any substituents are present, each substituent independently has a molecular weight of 15 g/mol to 500 g/mol.

17. The compound of claim 8, having a lowest unoccupied molecular orbital (LUMO) energy of about −2.5 eV to about −2.7 eV.

18. The compound of claim 1, having a highest occupied molecular orbital (HOMO) energy about −5.5 eV to about −5.8 eV.

19. The device of claim 14, wherein the compound is: